United States Patent
Bajema et al.

(10) Patent No.: US 10,801,979 B2
(45) Date of Patent: Oct. 13, 2020

(54) NMR-BASED NON-INVASIVE AND QUANTITATIVE FOOD ATTRIBUTE MEASUREMENT APPARATUS AND METHOD

(71) Applicant: Frito-Lay North America, Inc., Plano, TX (US)

(72) Inventors: Rick W. Bajema, Rhinelander, WI (US); Jason Ballengee, Dallas, TX (US); Kevin Minard, Kennewick, WA (US)

(73) Assignee: Frito-Lay North America, Inc., Plano, TX (US)

( * ) Notice: Subject to any disclaimer, the term of this patent is extended or adjusted under 35 U.S.C. 154(b) by 0 days.

(21) Appl. No.: 16/176,899

(22) Filed: Oct. 31, 2018

(65) Prior Publication Data
US 2019/0064086 A1 Feb. 28, 2019

Related U.S. Application Data

(62) Division of application No. 15/270,276, filed on Sep. 20, 2016.

(51) Int. Cl.
*G01N 24/08* (2006.01)
*G01N 33/02* (2006.01)

(52) U.S. Cl.
CPC ......... *G01N 24/082* (2013.01); *G01N 24/085* (2013.01); *G01N 33/02* (2013.01)

(58) Field of Classification Search
None
See application file for complete search history.

(56) References Cited

U.S. PATENT DOCUMENTS

| | | | |
|---|---|---|---|
| 2,999,381 A * | 9/1961 | Chope | G01R 33/46 73/73 |
| 3,966,973 A | 6/1976 | Henry | |
| 4,430,719 A * | 2/1984 | Pearson | F27D 19/00 432/37 |
| 4,701,705 A * | 10/1987 | Rollwitz | G01N 24/00 324/306 |
| 5,530,350 A | 6/1996 | Dechene | |
| 7,979,230 B2 * | 7/2011 | Dutton | G01F 25/0007 702/100 |
| 2002/0144458 A1 | 10/2002 | Hunter | |
| 2013/0154644 A1* | 6/2013 | Virtanen | G01N 24/08 324/309 |
| 2015/0168365 A1* | 6/2015 | Connor | G06F 19/3475 356/51 |

(Continued)

FOREIGN PATENT DOCUMENTS

GB 2497268 A * 6/2013 .......... G01N 27/023

*Primary Examiner* — Paresh Patel
(74) *Attorney, Agent, or Firm* — Barnes & Thornburg LLP; G. Peter Nichols

(57) ABSTRACT

A non-invasive NMR based apparatus for measuring a food attribute (moisture, sugar content) in food products comprises a magnetic chamber, an RF pulsing device attached to the magnetic chamber, a sensor receiver, and a data processing unit in communication with the sensor receiver. The pulsing device exposes the food ingredients/snacks to an RF field and produces an NMR response signal that is detected by the sensor receiver. The data processing unit quantitatively measures a food attribute of the food product based on the NMR response signal.

26 Claims, 13 Drawing Sheets

(56) References Cited

U.S. PATENT DOCUMENTS

2016/0140870 A1* 5/2016 Connor ............... G01N 21/255
                                                    356/51
2017/0089869 A1* 3/2017 Bai ..................... G01N 33/10

* cited by examiner

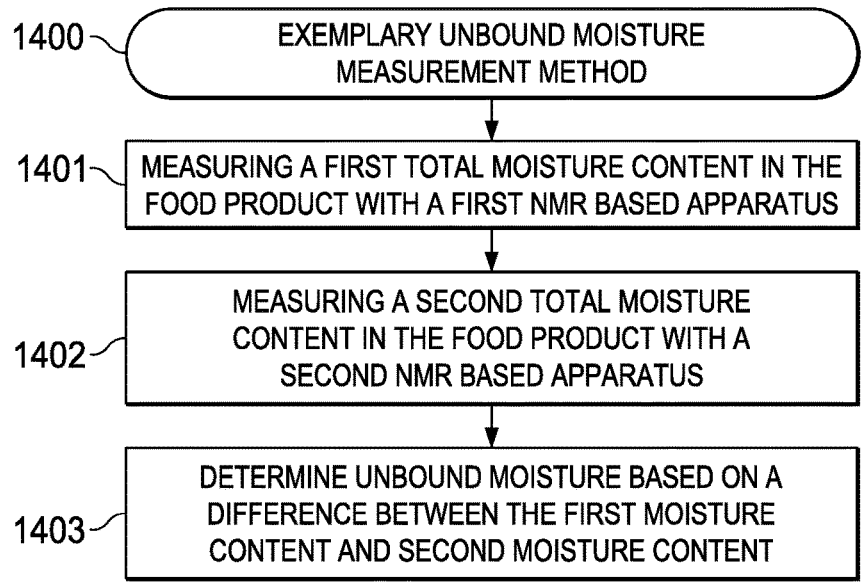
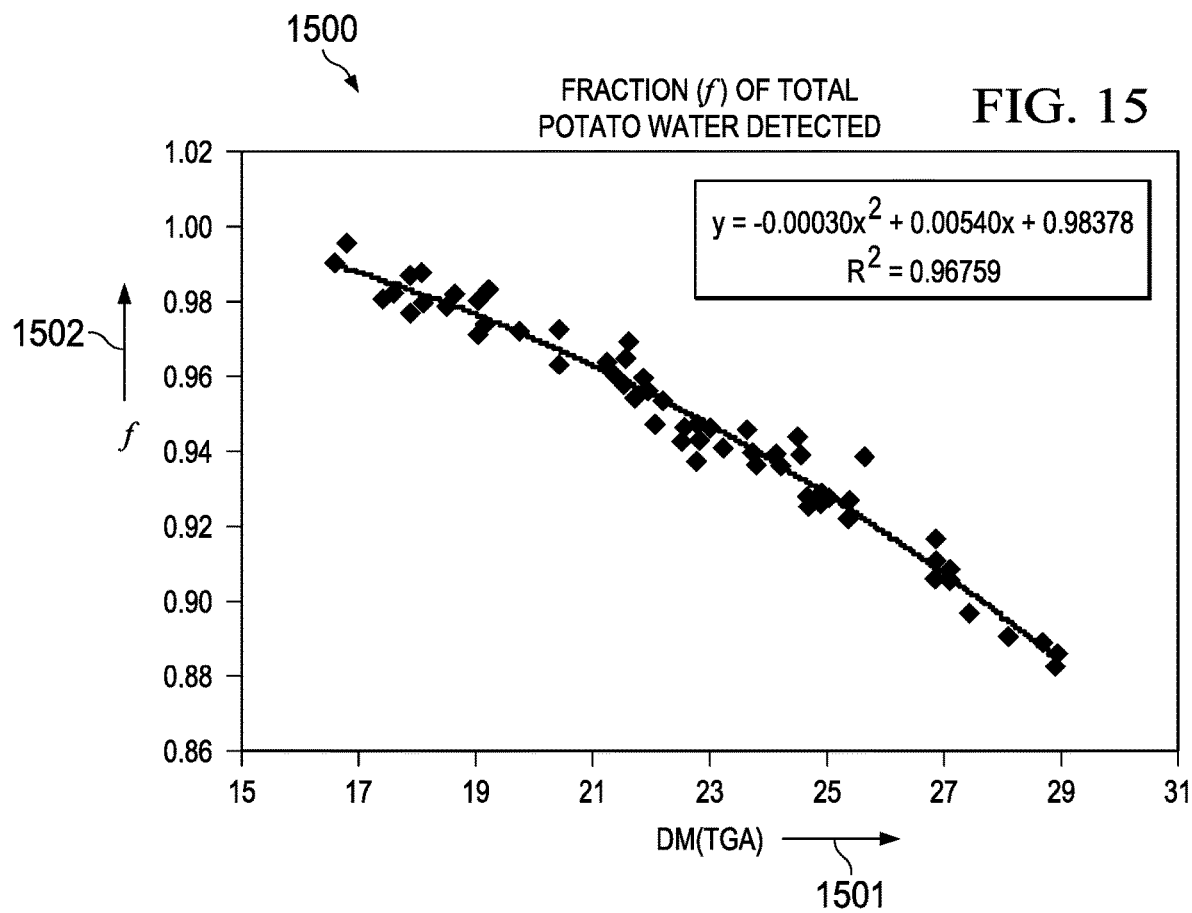

NMR-BASED NON-INVASIVE AND QUANTITATIVE FOOD ATTRIBUTE MEASUREMENT APPARATUS AND METHOD

CROSS-REFERENCE TO RELATED APPLICATION

This application is a divisional (DIV) of U.S. Ser. No. 15/270,276 filed Sep. 20, 2016, the disclosures and technology of which is hereby incorporated by reference.

The U.S. Government has rights in this invention pursuant to Agreement 67685 between Battelle Memorial Institute Pacific Northwest Division and PepsiCo.

FIELD OF THE INVENTION

The present invention relates to Low Field Nuclear Magnetic Resonance (LF-NMR) and its use for non-invasive quantitative measurements of moisture, solids, and sugar content in food products.

Prior Art and Background of the Invention

Prior Art Background

When a food snack such as potato chip is manufactured, food properties such as texture, crispiness, and hardness, are dependent on raw material characteristics (e.g. low solids or high solids potatoes, moisture content, sugar content). In particular, finished product characteristics (color, texture, flavor) are affected by raw material moisture and sugar variability.

The crispiness, softness and/or crunchiness of a potato chip are just a few examples of food snack characteristics that make food appealing and satisfying to consumers. Texture and flavor are some of the criteria which consumers use to judge the quality and freshness of many foods. When a food produces a physical sensation in the mouth (hard, soft, crisp, moist, dry), the consumer has a basis for determining the food's quality (fresh, stale, tender, ripe).

Currently, it is a major challenge to accurately measure the moisture content of raw materials. It is not feasible to determine the chemical composition, most notably the moisture content, of a reasonable sample size (e.g., >1 wt. %) of incoming foodstuffs or any related raw materials used for manufacturing processed foods. Because of this inability to determine moisture levels, prior art systems and methods cannot operate food processing equipment at optimal efficiency. Furthermore, it is not currently practical to sort many incoming foodstuffs based on their moisture content into separate processing batches (e.g., sort and process all foodstuffs between 18% and 20% moisture, and between 20% and 22% moisture separately). Processing optimization for maximum product quality is therefore not possible and there is an ongoing need for rapid measurements on whole, raw foodstuffs in an entirely non-invasive manner.

Prior Art Food Snack Manufacturing System (0100)

As illustrated in FIG. 1, a prior art food snack manufacturing system comprises a series of apparatus that include a sourcing stage (0101), storage station (0102), wash/peel station (0103), slicing station (0104), frying station (0105), inspection station (0106), seasoning station (0107), and a packaging station (0108). The food snacks, such as potato chips, may be conveyed from station to station on a conveyor belt during the manufacturing system.

Prior Art Food Snack Manufacturing Method (0200)

As generally shown in FIG. 2, a prior art manufacturing method associated with the prior art system in FIG. 1 may include the steps comprising:

(1) Sourcing food ingredients (0201);

Ingredients for food snacks, for example, potatoes may be sourced from different farms. The potatoes may have different moisture/solids content depending on the farms. There is therefore a need for an apparatus to measure and to differentiate food ingredients so that downstream processing may be optimized based on the food attribute such as moisture and/or solids content. The pricing and grading for food ingredient or raw materials may be based on the input quality and moisture/solids percentage. Therefore, there needs to be an apparatus to quantitatively measure moisture/solids percentage in incoming food raw materials. There is also a need to provide a non-invasive quantitative apparatus at the receiving area, storage area, on the farm where the food raw materials are grown, or at the off-site food storage locations.

(2) Storing food ingredients (0202);

When the potatoes arrive at the plant, they are examined for quality. A quick fry may be performed in the receiving area (batch) in some countries to check for sugars, etc. The method provides a qualitative indicator of sugar level, but is not a good way to control a process.

The current method of determining moisture and solids percentage is typically based on specific gravity measurements that are performed on a very small percentage of incoming raw materials. This method is prone to error, lacks statistical resolution of the entire load of potatoes, and is sometimes time consuming.

After inspection, the potatoes are loaded into a vertical helical screw conveyer which allows stones to fall to the bottom and pushes the potatoes up to a conveyer belt to the automatic peeling machine. After they have been peeled, the potatoes are washed with cold water. The peeling process may introduce a change of moisture or solid content (percentage) in the potatoes. Therefore there is a need to provide a non-invasive quantitative food attribute (moisture/solid content) measuring apparatus in line after a unit operation such as peeling.

(3) Processing food ingredients (0203);

The potatoes pass through a slicer that cuts them into slices. The slices fall into a second cold-water wash that removes the starch released when the potatoes are cut. The slices pass under air jets that remove excess water as they flow into troughs filled with oil. The oil temperature is kept at a certain temperature. Paddles gently push the slices along. After emerging from the oil, the fried chips are tumbled, and salt is sprinkled from receptacles positioned above the chips. Moisture may be measured on these chips and a heat/mass balance may be used to determine the energy input required to drive the moisture down to a desired point. The manufacturing system predicts the incoming water based on literature or measured values for raw potatoes, and the processing conditions are adjusted to meet a desired finished moisture content. There is a need for a more inline method and apparatus to determine the moisture loss during such processing.

(4) Inspecting food snack for quality (0204);

At the end of the trough, a wire mesh belt pulls out the hot chips. As the chips move along the mesh conveyer belt, excess oil is drained off and the chips begin to cool. They then move under an optical sorter that picks out any burnt slices and removes them with puffs of air. The potato chips are inspected for texture, flavor, and mouthfeel by using a qualitative tasting process.

(5) Determining if the quality is acceptable, if so, proceeding to step (0208);

Taste samples are made from each batch throughout the manufacturing process, usually at a rate of once per hour. The tasters check the chips for salt, seasoning, moisture, color, and overall flavor. Color is compared to charts that show acceptable chip colors. Texture is also qualitatively determined by tasters as compared to a reference sample. There is a need for an automated in-line food attribute measurement apparatus to provide an automatic continuous closed loop feedback to control input parameters of the processing step of the manufacturing process. Final food attributes such as texture, flavor, starch content, etc. are not controlled unless the moisture content is controlled at each stage of the unit operations.

(6) If food quality is not acceptable, rejecting the food snack, proceeding to step (0207);

(7) Manually adjusting process parameters and proceeding to step (0203);

The process parameters are adjusted manually. Therefore, there needs to be an automatic feedback process that adjusts the input parameters to adjust the output quality such as texture attributes which include hardness, fracturability and denseness, flavor, starch content, mouth feel.

(8) Accepting the food snack (0208).

Prior Art Moisture/Solids Measurement Method

As generally shown in FIG. 3, a prior art in-line moisture/solids measurement method may include the steps comprising:

(1) Measuring known high solid content potatoes and known low solid content potatoes (0301);
(2) Measuring specific gravity of the high and low solid potatoes (0302);
(3) Generating an empirical equation for moisture content based on regression (0303); and
(4) Measuring additional potatoes of unknown solid content and inferring moisture content based on the predictive equation formulated in step 3 (0304).

The above method for determining moisture is prone to variability. Generated data generally lacks granularity or statistical resolution, and predictions are based on a very small sample relative to the total material of interest. Therefore, there is a need for a precise and accurate measurement method to quantitatively measure moisture and solid content attributes. Similarly, sugars are currently measured using low sampling-rate wet chemistry methods that are precise and specific, but are time-consuming, tedious, and labor intensive.

BRIEF SUMMARY OF THE INVENTION

The present invention in various embodiments addresses one or more of the above objectives in the following manner. A non-invasive LF-NMR based apparatus for measuring a food attribute (moisture, sugar content) in food products comprises a magnetic chamber, a pulsing device attached to the magnetic chamber, a sensor receiver interior to the magnetic chamber, and a data processing unit in communication with the sensor receiver. The pulsing device exposes the food ingredients/snacks to an RF pulse that produces an NMR response signal detected by the sensor receiver. The data processing unit quantitatively measures a food attribute of the food product based on the NMR response signal. A feedback and feedforward system and method for continuously controlling food properties of food snacks in a manufacturing process includes an NMR based apparatus that is positioned inline with other unit operations. A controller adjusts processing parameters to a food processing unit based on the information from the NMR apparatus such that the final food attribute of a resultant food snack falls within an acceptable limit.

The present invention apparatus may be utilized for noninvasively measuring a food attribute of a food product using a method comprised of the steps of:
 a) presenting a food product on a surface;
 b) polarizing the nuclear magnetic moments inside the food product during residence in a magnetic chamber;
 c) exposing the food product to an RF pulse;
 d) generating an NMR response signal from the food product;
 e) capturing and forwarding the NMR signal to a data processing unit; and
 f) measuring the food attribute of the food product with the data processing unit.

Integration of this and other preferred exemplary embodiment methods in conjunction with a variety of preferred exemplary embodiment systems described herein in anticipation by the overall scope of the present invention.

BRIEF DESCRIPTION OF THE DRAWINGS

For a fuller understanding of the advantages provided by the invention, reference should be made to the following detailed description together with the accompanying drawings wherein:

FIG. 14 is an exemplary unbound moisture measurement method according to a preferred embodiment of the present invention.

FIG. 15 is an exemplary chart of fraction of detectable water vs dry matter in a food product according to a preferred embodiment of the present invention.

DESCRIPTION OF THE PRESENTLY EXEMPLARY EMBODIMENTS

Figure 1:
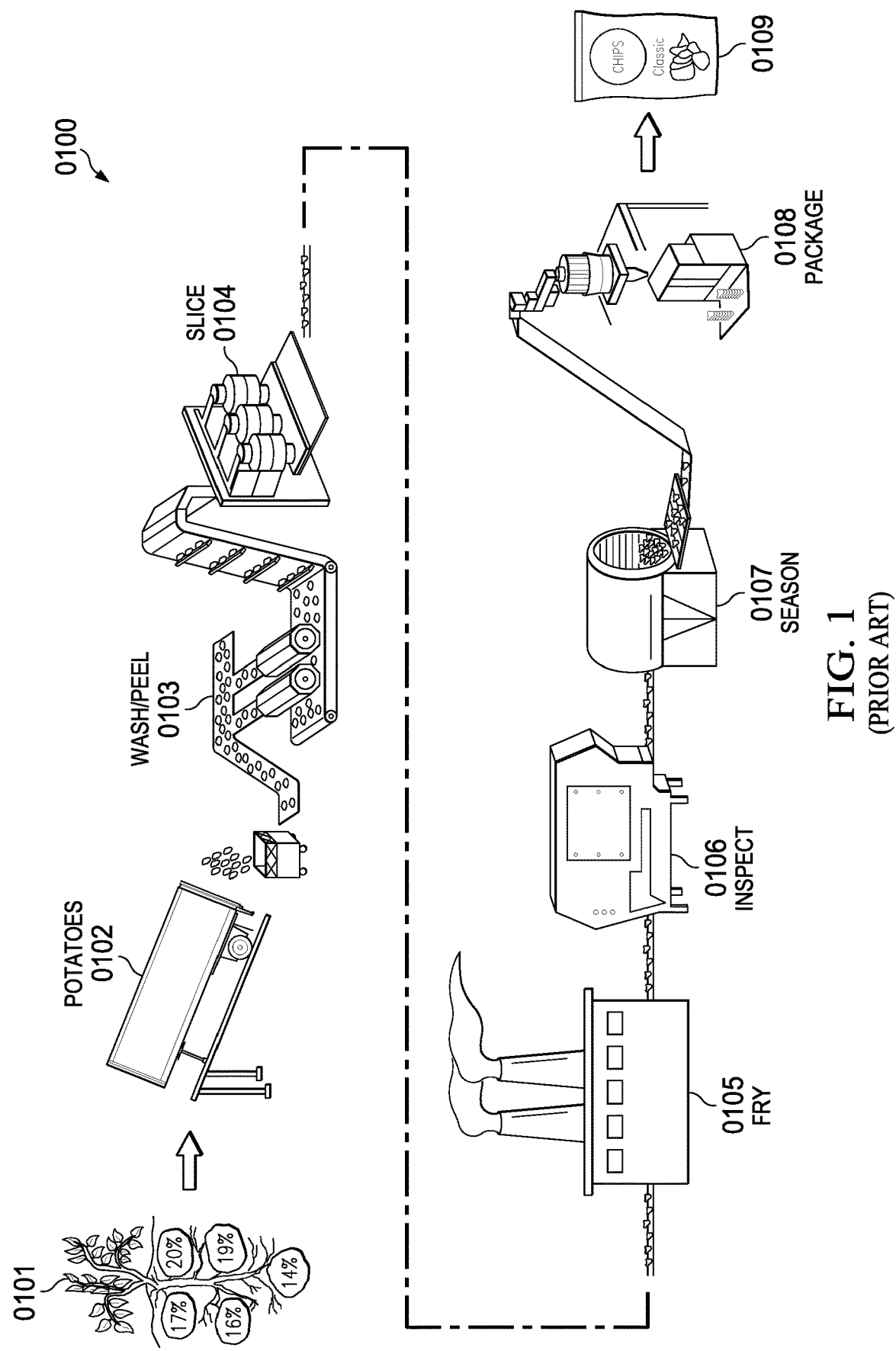
FIG. 1 is a prior art food product manufacturing system.
Figure 2:
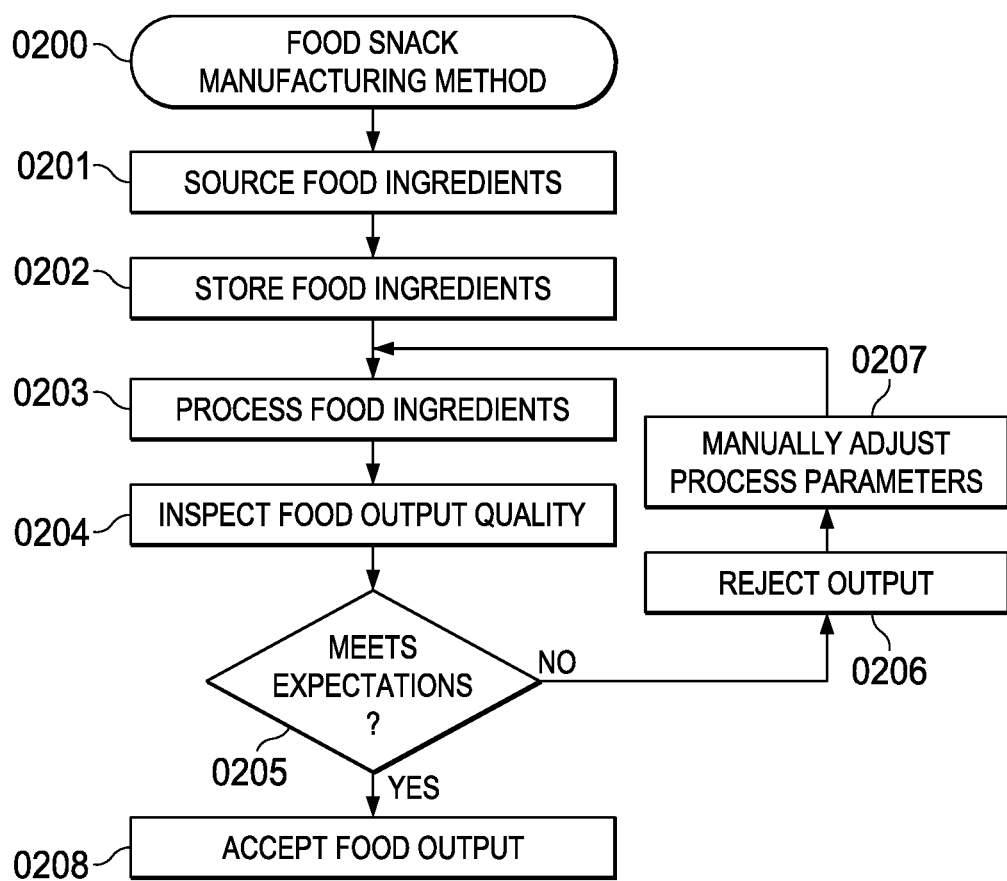
FIG. 2 is a prior art food product manufacturing method.
Figure 3:
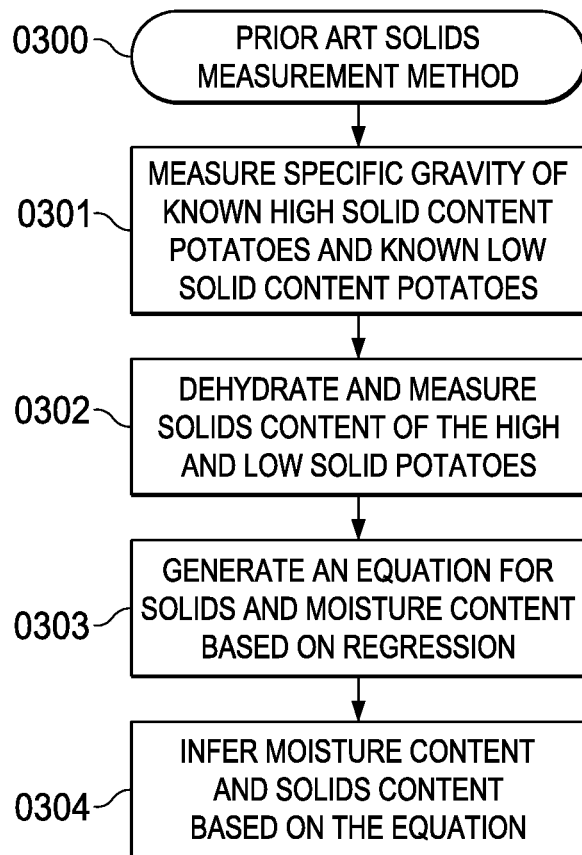
FIG. 3 is a prior art food attribute measurement method.

While this invention is susceptible to embodiment in many different forms, there is shown in the drawings and will herein be described in detail, a preferred embodiment of the invention with the understanding that the present disclosure is to be considered as an exemplification of the principles of the invention and is not intended to limit the broad aspect of the invention to the embodiment illustrated.

The teachings of the present application will be described with particular reference to the present exemplary embodiment, wherein these innovative teachings, both apparatus and method, are advantageously applied to quantitative measurement of food attributes for foods and food snacks. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Current objective methods to measure moisture are limited in detecting moisture changes of a small magnitude with an acceptable degree of accuracy and require several measurements of the same substrate to differentiate slightly different substrates with statistical significance.

Consequently, there is a need for a non-invasive quantitative food attribute measurement that accomplishes the following objectives:

Provide for quantitative analytical measurement of food attributes such as moisture and solids content.
Provide for non-invasive method for measuring solids and moisture content without immersion in liquid media.
Provide for quantitative test for moisture measurement for a whole raw food ingredient such as a whole potato.
Provide for quantitative measurement of moisture and solids with greater accuracy reliability, and speed.
Provide for a stand-alone quantitative food attribute measurement apparatus deployed at a farm or an off-site food storage facility.
Provide for measurement of absolute moisture content without the use of an inferred empirical method.
Provide for a feedforward system that predicts food snack output attribute based on input food ingredient properties such as moisture and solids content.
Provide for high resolution moisture measurement with better than 5% accuracy.
Provide for repeatable and reproducible quantitative measurements of food attributes.
Provide for an automated method for measuring moisture and solids content.
Provide for a method of estimating sugar content.
Provide for a method of measuring bound vs. unbound water.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

It should be noted that the terms "NMR based apparatus," "NMR quantitative tool," and "NMR based quantitative apparatus" as used herein are used inter-changeably to indicate a tool used to measure a food property in a food snack or food ingredient, such as moisture and sugar content, based on an NMR signal. It should be noted that the terms as used herein "moisture content" and "moisture" is used to indicate absolute amount of moisture in a food snack, food ingredient or a raw material. It should be noted that the term as used herein "moisture percentage" is used to indicate a percentage by weight of moisture in a food snack, food ingredient or a raw material. It should be noted that the terms as used herein "solids percentage", "dry matter percentage", "starch percentage", and "sugars percentage" are used interchangeably to indicate a percentage by weight of content other than moisture present in a food product, food snack, food ingredient, or a raw material. The sugars referred to herein may be reducing sugars or total sugars.

The field of LF-NMR relaxometry is already well established for identifying different molecular species and studying their dynamics in complex materials. A general approach involves NMR measurements of relaxation times that govern the temporal behavior of NMR signal like shown in FIG. 7 and FIG. 11. Results are of general interest because the strength of NMR signal gives quantitative information about the amount of detected materials, and NMR relaxation is highly sensitive to the molecular environment where NMR signal originates. The most commonly measured relaxation times are T1 and T2. The first defines how fast (longitudinal) magnetization approaches thermal equilibrium after a sample is exposed to an external magnetic field, and the second defines how fast magnetization decays after an applied RF field rotates longitudinal magnetization by 90° into the transverse (detection) plane. Based on these well-known definitions, T1 and T2 are often referred to as longitudinal and transverse relaxation times. Generally, measured values for T2 are sensitive to time-averaged molecular behavior, whereas T1 is sensitive to faster molecular dynamics. In both cases, measured values depend on chemical species and mobility. Thus, in complex systems, sample heterogeneity gives rise to a distribution of relaxation times that can be measured using either one dimensional (1D) or multidimensional (nD) techniques. 1D measurements generally monitor NMR signal evolution under the influence of a single relaxation mechanism (i.e. T1 or T2), whereas, signal in nD experiments evolves under two or more. Today, these underlying principles and methods are commonly exploited by benchtop LF-NMR systems that are widely employed for non-destructive testing in the food, polymer, petroleum, and pharmaceutical industries. Common applications include the determination of solid-to-liquid and oil-to-water ratios in materials as diverse as oil-bearing rock, food emulsions, and plant seeds. A major limitation is that no commercial benchtop LF-NMR systems are large enough to accommodate larger samples such as whole potatoes. They are also not properly configured for conveyor integration or the routine washing needed for maintaining industrial hygiene standards. The present invention generally overcomes these common obstacles to enable the broader use of LF-NMR in the food processing industry.

One aspect of the present invention provides an analytical method to quantitatively measure the amount of moisture and/or solids in a food snack or its raw material. Another aspect of the present invention includes a method to empirically predict a food attribute based on NMR relaxation measurements and other input from more traditional sensors. Another aspect of the present invention includes a closed loop feedback system for continuously controlling output food attributes of a food snack such as texture, flavor, and mouthfeel in a manufacturing process. Yet another aspect of the present invention includes a closed loop feedback system and an open loop feedforward system for continuously controlling output food attributes of a food snack such as texture, flavor, and mouthfeel of a food snack in a manufacturing process.

Applicants herein have created an apparatus positioned in a manufacturing system. The apparatus comprises a magnetic chamber for magnetizing/polarizing a food snack, a pulsing tool for applying RF fields to a food snack, a sensor receiver for recording/capturing the excited NMR signal from the food snack, and a data processing unit that processes the captured NMR signal. In one embodiment, the pulsing tool is an RF generating tool that is configured to generate an RF pulse. There are a number of embodiments of this invention which fall within the scope of the invention in its broadest sense.

Figure 4:
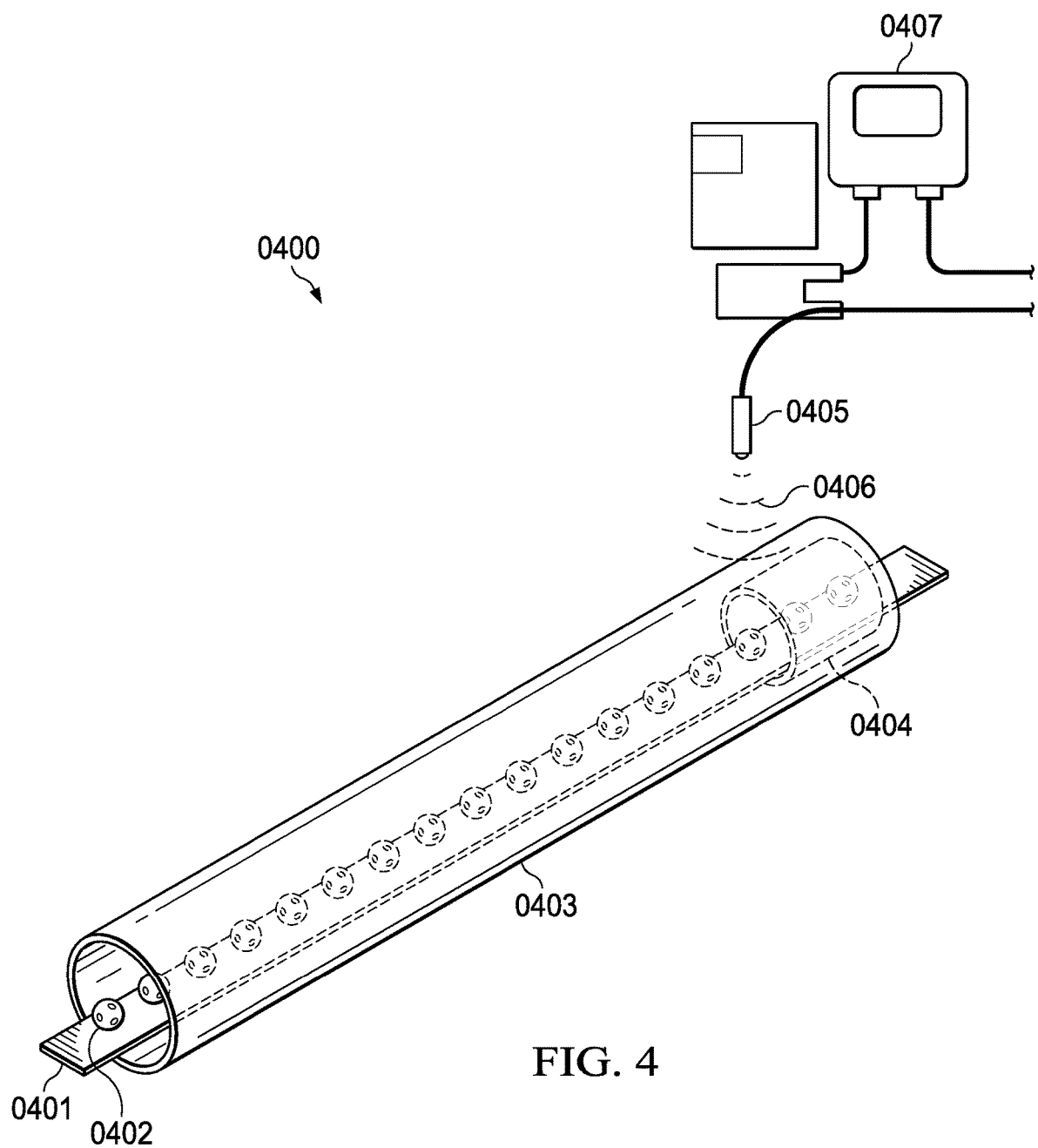
FIG. 4 is an NMR based apparatus for quantitative measurement of a food attribute according to an exemplary embodiment of the present invention.

The present invention may be seen in more detail as generally illustrated in FIG. 4, wherein an exemplary NMR based food property measuring apparatus (0400) comprises a magnetic chamber (0403), a radio frequency (RF) pulsing device (0404) that may or may not be attached to the magnetic chamber and exposes a food product or ingredient (0402) to RF fields, a staging station that moves and positions food products (0401), a sensor receiver (0405) that captures an NMR signal (0406), and a data processing unit (0407) to process the captured NMR signal. The sensor receiver (0405) and the pulsing device (0404) may be the same and integrated as an RF probe. The apparatus of FIG. 4 may further be integrated with non-NMR sensors selected from a group comprising: infrared, microwave, ultraviolet, visible light, mass, volume, or temperature sensors. The RF probe may expose the food products to an RF pulse and also capture an NMR signal from the food products. The food staging station may be movable such as conveyor or a non-movable surface. In another embodiment, objects or food may free fall through the NMR device. The shape of the magnetic chamber may be a hollow tubular or cylindrical form among other possible geometries. The magnetic chamber may be designed with current carrying wire or permanently magnetized material that is intentionally configured with geometries to expose the food product to a static magnetic field. According to a preferred exemplary embodiment, the magnetic chamber comprises one or more regions of differing magnetic strengths. According to another preferred exemplary embodiment, the magnetic chamber comprises one or more magnets. The overall apparatus may be miniaturized to fit a footprint of a manufacturing line. According to a preferred exemplary embodiment, multiple apparatus or units may be configured in a parallel fashion to substantially increase the throughput of food processing. According to another preferred exemplary embodiment, multiple units or apparatuses such as in apparatus (0400) may work in series to characterize changes in food products during processing along a manufacturing line.

According to a preferred exemplary embodiment, the pulsing tool is an RF generating unit that generates a pulsed RF field. The staging station (0401) may be a conveyor belt carrying the food snacks/ingredients, when an input attribute such as moisture or solids content is measured in a manufacturing process on-line. For example, the staging station may carry potatoes spaced equally or unequally as illustrated in FIG. 4. The speed of the conveyor may be adjusted to limit the time a food snack resides in the magnetic chamber. In one preferred embodiment, the staging station (conveyor) may be moving at a speed in the range of 2 ft/min to 100 ft/min. According to a preferred exemplary embodiment, the (polarization) time in the magnetic chamber may range from 0.3 secs to 5 secs. According to a more preferred exemplary embodiment, the (polarization) time in the magnetic chamber may range from 1.5 secs to 2 secs. The staging station may carry a raw food or finished food snack such as tortilla chips, potato chips, oat based products, corn products, non-starch-based food snacks, any starch-based finished edible food snacks, legumes, pulses, cut fruit, whole fruit, tubers, vegetables or seafood. The magnetic chamber is configured to polarize food products passing within. The magnetic chamber may be composed of one or more permanent magnets or electromagnets. When an electromagnet is used, the current passing through the magnet may be measured. The measured current can then be used to correct for any deviation in the current flow. Sample polarization is generally determined by the amount of hydrogen atoms in the food product. The concentration of hydrogen as measured in the captured NMR signal may be directly related to the moisture and solid content in the food product. All the hydrogen in the food product is polarized, but hydrogen NMR signal from solids and liquids will decay at different rates to facilitate confident differentiation. According to a preferred embodiment, the signal from the hydrogen in liquids is captured. Another preferred embodiment captures the solid signal or both solid and liquid. The direction of magnetic flux from the magnetic chamber may generally be transverse or parallel to the movement of the staging station. According to a preferred exemplary embodiment, the static magnetic field strength may range from 1 to 6000 Gauss. According to a more preferred exemplary embodiment, the magnetic strength may range from 70 Gauss to 3000 Gauss. The sensor device may capture signal at or near the Larmor frequencies of captured NMR signal. Therefore, the RF pulse frequency is adjusted depending on magnetic field strength. The pulse may be centered around the Larmor frequency or offset for spatial localization in conjunction with magnetic field gradients (i.e. imaging). According to an exemplary embodiment, the sensor receiver (0405) may be positioned to record/capture an NMR signal (0406) from the food snack (0402). The sensor receiver (0405) may be in communication with a data processing unit (DPU) (0407) via a cable or wirelessly without a cable. The sensing device may capture the NMR signal across a wide range of time periods or from multiple distinguished sample regions. According to a preferred exemplary embodiment a distance between the signal sensing device and the food product may range from 0.0 inch to 2 feet. The sensor receiver may be in communication with a data processing unit. To eliminate RF interference and potential RF exposure hazards for nearby personnel, the magnetic chamber may function as a Faraday cage, and the RF pulsing device may also be surrounded by a conducting screen.

The sensor receiver (0405) may be connected physically with a conducting cable to the DPU (0407) via an input-output module in the DPU (0407). In an alternate arrangement, the sensor receiver (0405) may forward the NMR signal to the input-output module in the DPU (0407) wirelessly. The wireless protocol may use standard protocols such as LTE, 3G, 4G, WIFI, or Bluetooth. In another exemplary embodiment, the remotely located DPU (0407) may be connected to the sensing device (0405) with wired protocol such as Ethernet.

The NMR signal (0406) may then be captured for a period of time. The NMR signal (0406) may be represented as NMR signal strength (a.u.) vs. time (secs) as generally illustrated in FIG. 7. According to a preferred exemplary embodiment, the NMR signal is captured for 0.01 sec to 3 minutes. According to a more preferred exemplary embodiment, the NMR signal from the food product is captured for 0.2 sec to 5 sec. According to a most preferred exemplary embodiment, the NMR signal from the food snack is captured for about 1 sec or less.

According to a preferred exemplary embodiment, the pulsing tool directs RF towards the food snack for a pulse duration typically for a fraction of a second. According to a most preferred exemplary embodiment, the pulsing tool directs RF towards the food snack for a pulse duration of 1 microsecond to 10 milliseconds. The frequency and phase of the RF pulsing tool is also adjustable to allow for precise generation and manipulation of NMR signal. The food product remains intact after RF fields are applied and the NMR signal detected.

Figure 5:
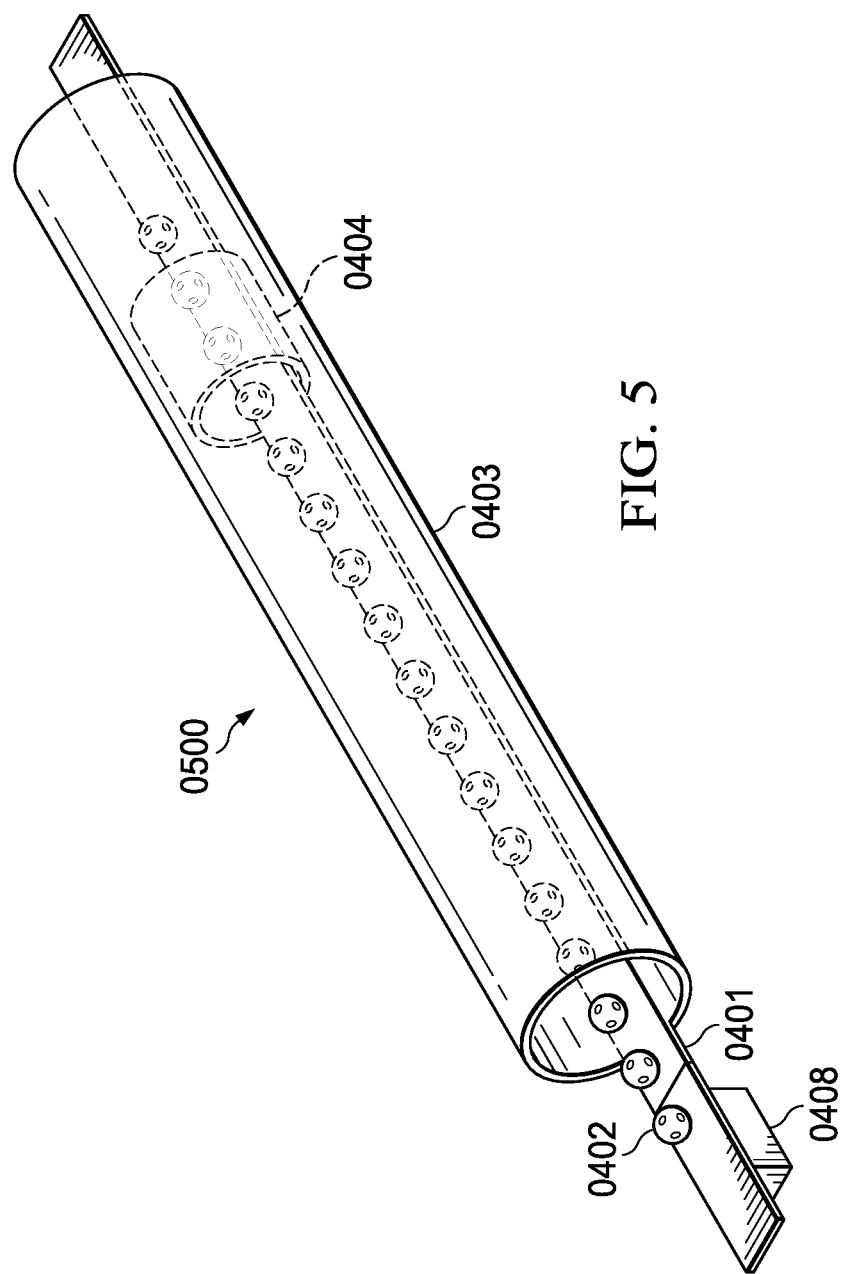
FIG. 5 is an NMR based apparatus with a mass flow device or other type of existing sensor for quantitative measurement of a food attribute according to an exemplary embodiment of the present invention.

The exemplary NMR based apparatus illustrated in FIG. 4 may further comprise a mass flow device (0408) or some other type of standard sensor as illustrated in FIG. 5 (0500). If a mass flow device is employed (0408) it may be used in conjunction with apparatus (0400) to determine the total mass of the food product. The mass flow device can be positioned upstream, downstream, or within the NMR apparatus. The positioning of the mass flow device is based on the foot print and the logistics of the unit operations. The device (0408) may also be a volume flow device according to an alternate embodiment. The volume flow device may further measure a volume of the food product and a mass may be estimated based on the measured or assumed specific gravity using any commonly available methods. Alternate embodiments might employ alternative sensing technology based on infrared or near infrared spectroscopy, visible light, ultrasonics, electrical impedance and the like.

Figure 7A:
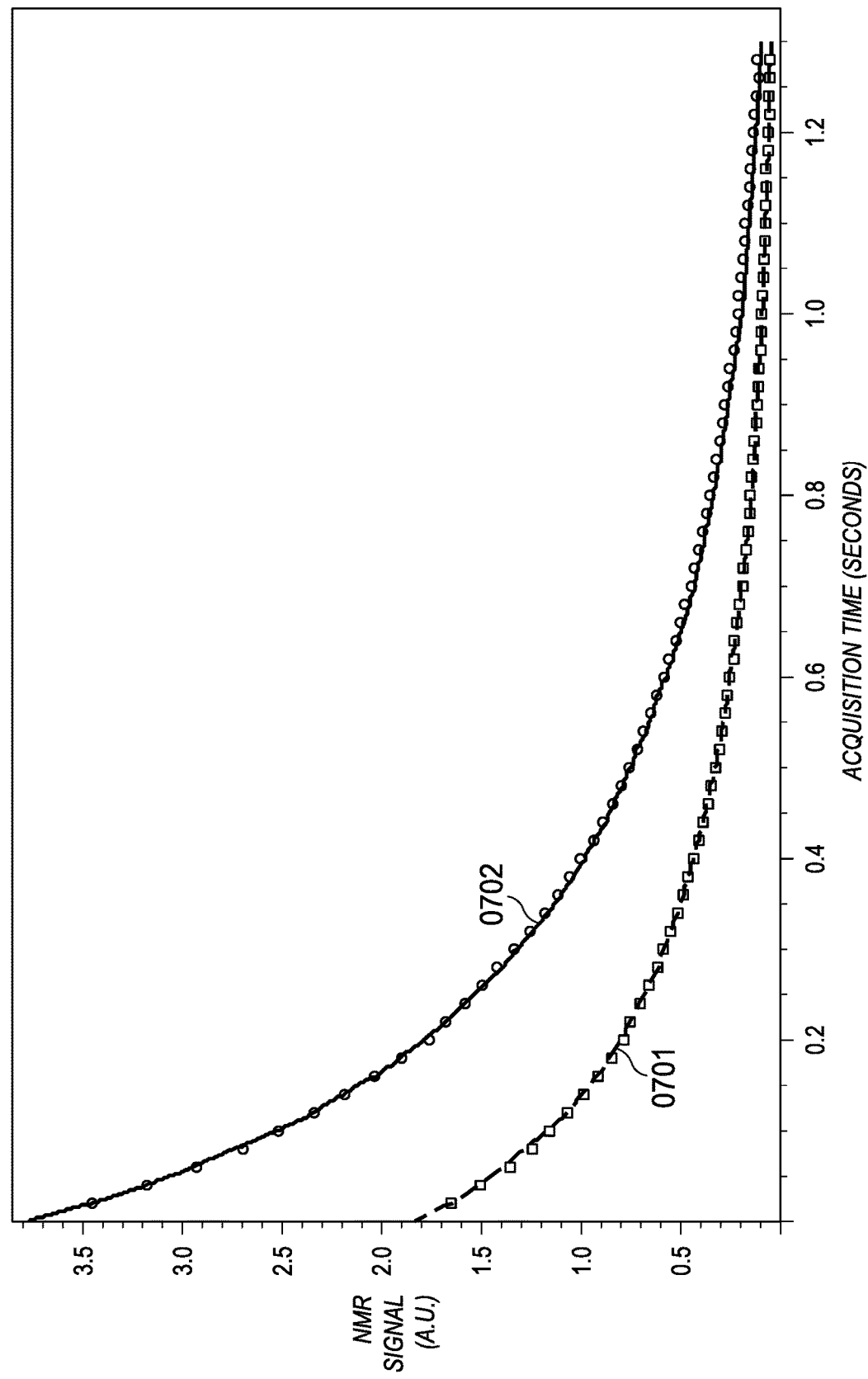
FIG. 7*a* is a chart of a captured NMR signal from an NMR apparatus according to an exemplary embodiment of the present invention.

FIG. 7a illustrates typical NMR signal captured for two potatoes with the NMR apparatus described in FIG. 4 (0400). Decay curves (0701) and (0702) represent NMR signals from two potatoes with a high and low solids content respectively. The NMR signal generated from the apparatus may be represented by an equation (1) as described below $$S(t)=A1e^{-t/B1}+A2e^{-t/B2}+\text{Noise}. \quad (1)$$

Here, S is the NMR signal as function of time (t), A1, A2 are two signal amplitudes and B1, B2 are two (transverse) decay times for water in two different micro-environments.

In practice, signal amplitudes and decay times may be determined based on the decay curve. A1, A2, B1, B2 are positive numbers or decimals that are easily determined by fitting measured data to equation (1). To formulate an empirical approach for predicting food attributes, a database of parameters that include time constants (B1, B2) and amplitudes (A1, A2) may be generated from NMR signals captured for potatoes or food products with known food attributes like solids or moisture content. The captured NMR signals may be smoothed, filtered and regressed to determine the time constants and the amplitudes as a function of known food attributes like dry matter or moisture content. The measured data can then be used to generate a linear or higher order model that predicts food attributes from NMR parameters measured from uncharacterized potatoes or food products. If a linear prediction model is employed, estimates of food attributes like moisture or sugar may take the following form $$\text{Food Attribute NMR Prediction}=C1*A1+C2*A2+C3*B1+C4*B2 \quad (2)$$

Figure 7B:
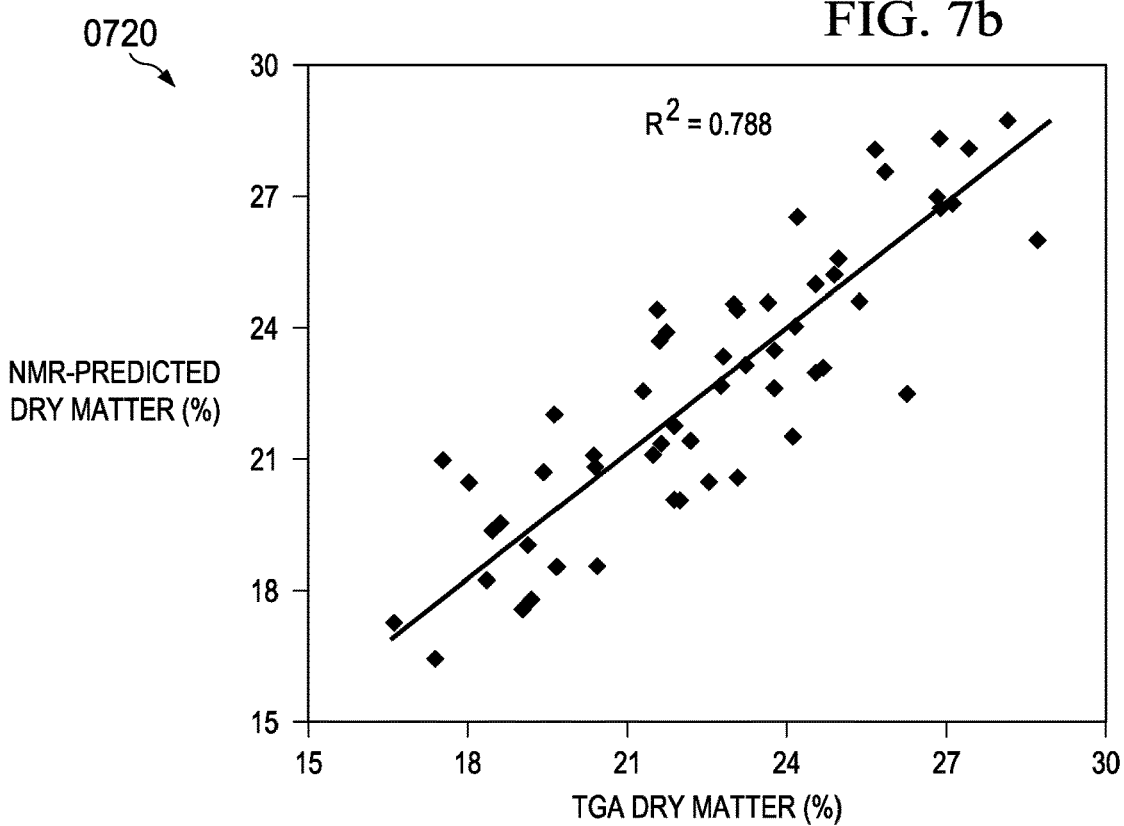
FIG. 7*b* is a chart of NMR predictions dry matter based on a prediction equation according to an exemplary embodiment of the present invention.
Figure 7C:
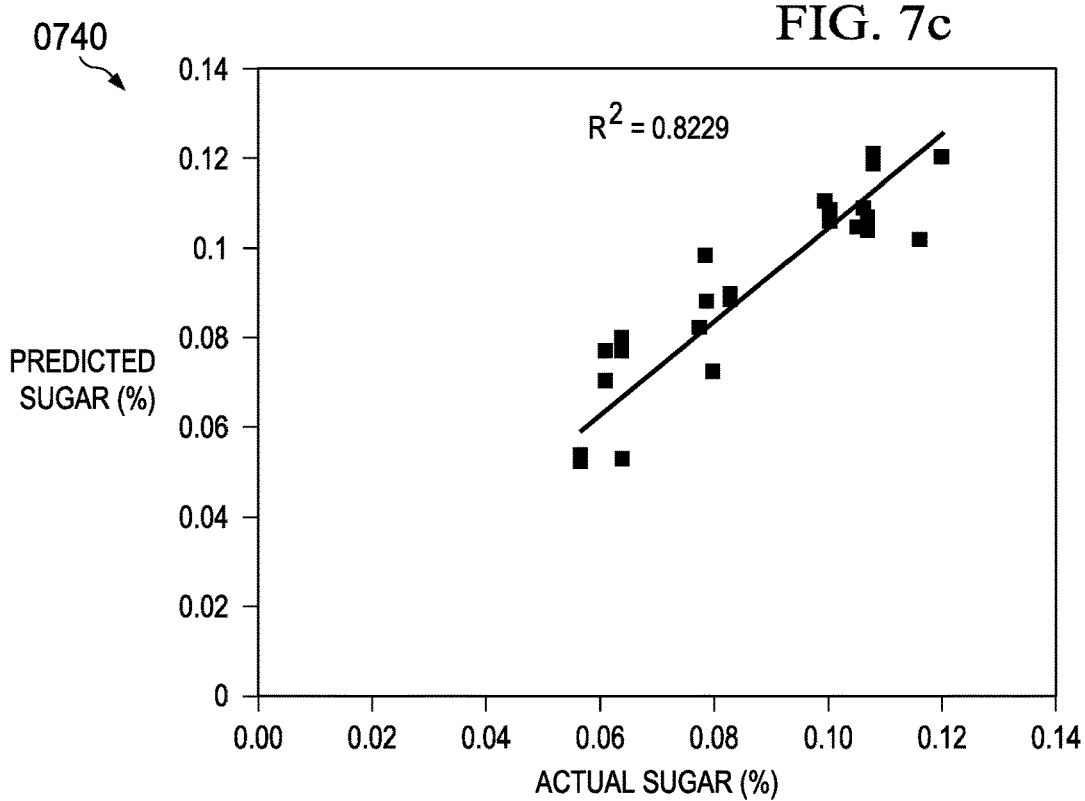
FIG. 7*c* is a chart of NMR predictions sugar based on a prediction equation according to an exemplary embodiment of the present invention.

Here, C1-C4 are modeling parameters derived from multivariate linear regression analysis of the measured database. Those skilled in the art will also recognize that Equation 2 can be readily modified to include non-linear prediction terms. Example predictions of moisture and sugar predictions, based on equation 2, are shown in FIGS. 7b and 7c respectively. FIG. 7b (0720) is an exemplary correlation between NMR based predictions of potato dry matter and actual values measured with Thermo-Gravimetric Analysis (TGA). Plotted predictions employ the apparatus of FIG. 4 and are formulated using only NMR parameters. This should be contrasted with FIG. 8 where results are formulated using additional information about potato weight. FIG. 7c (0740) is an exemplary correlation between NMR based predictions of total potato sugar and actual values measured with High Performance Liquid Chromatography (HPLC). Plotted predictions employ the apparatus of FIG. 4 and are formulated using only NMR parameters.

Figure 8:
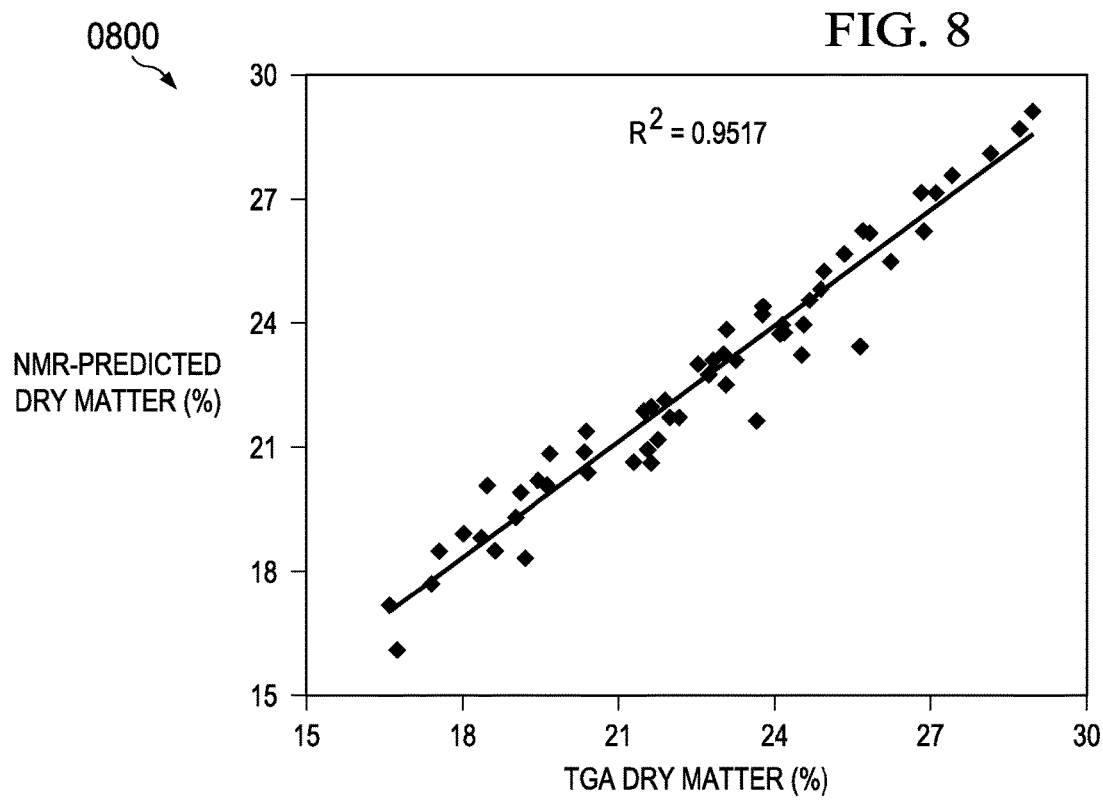
FIG. 8 is an exemplary correlation of potato dry matter measured by an NMR based apparatus to dry matter measured with a Thermo-Gravimetric Analysis (TGA). NMR based predictions are formulated using potato weight and the apparatus of FIG. 5.

More generally, multivariate (empirical) predictions might include information such as potato weight when measured values are determined from other sensors. The use of potato weight together with NMR is illustrated in FIG. 8. Typical embodiments are therefore not limited to a single multivariate approach but encompass all known prediction methods as well as multiple sensor modalities that include LF-NMR. It is also recognized that equation (1) is a simplification of NMR signal that can be expressed more generally as finite or continuous sum of decaying exponentials giving rise to the following equivalent signal representations $$S(t)=\Sigma A_i e^{-t/B_i}+\text{Noise}, \quad (3) \text{ and}$$

$$S=\int A(B)e^{-t/B}\,dB \quad (4)$$

Besides the above empirical approaches, it is also possible to implement analytical methods. Suppose, for example, another type of NMR signal having a different temporal behavior is measured. With this approach, collected NMR signal S(t), as in equation (5), depends on each potato's total water mass ($A_{total}$), its longitudinal relaxation time (C5), and the transit time through the magnet (α). Percent moisture predictions can then be made as in equation (6). In this case, coefficients C6, and C7 may be determined based on statistical regressions and analysis of NMR data collected using standard samples with known water content. The calculation of % moisture in Eq. (6) is then completed using the measured weight (Mass) of the food product or raw ingredient. The analytical use of NMR therefore provides a direct measurement of moisture weight, whereas, the total weight of moisture and solids is captured using standard gravimetric methods.

$$S(t=0)=(1-e^{-\alpha/C5})(A_{total})+\text{Noise} \quad (5)$$

$$\text{\% Moisture NMR Prediction}=(C6+C7*(A_{total}))/\text{Mass} \quad (6)$$

FIG. 8 (0800) generally illustrates an exemplary correlation between potato dry matter predicted by an NMR-based apparatus and dry matter measured using an 'industry standard' analytical approach called Thermo-Gravimetric Analysis (TGA). The NMR predictions on the y-axis are formulated using a linear multivariate model that is similar to equation 2 but also includes potato mass. The $R^2$ of the correlation illustrated in FIG. 8 is greater than 0.95. This is a remarkable result considering that NMR analysis is near real-time and is performed on whole intact potatoes. Conversely, typical TGA requires labor-intensive processing of whole potatoes to ensure efficient moisture evaporation, and even with this pre-processing, subsequent TGA measurements normally take more than two hours to complete.

The NMR sensor system enables a measurement of potato dry matter in a more precise and accurate method as compared to measuring specific gravity and dehydrating. The fundamental disadvantage in using the specific gravity and dehydrating method is that these methods are not easily incorporated into an entirely non-invasive online system. Furthermore, specific gravity measurements are susceptible to the amount of entrapped air inside the potato.

The apparatus of FIG. 0500) has several advantages over the apparatus of FIG. (0400). For example, more time is generally required to measure the NMR signal of equations (1), (3), and (4), and this can limit throughput for empirical predictions based on data from the apparatus of FIG. 0040). However, an initial reading for a shorter duration may be used in conjunction with equations (5) and (6) to analytically determine moisture content when using apparatus (0500). In this case, the dry matter content may be calculated from equation (6) using the total mass as measured by the mass flow device (0408). Therefore, it is not necessary to measure the entire NMR signal decay, and because of this, sensor throughput can be dramatically increased to greater than 5000 measurements an hour.

Figure 6:
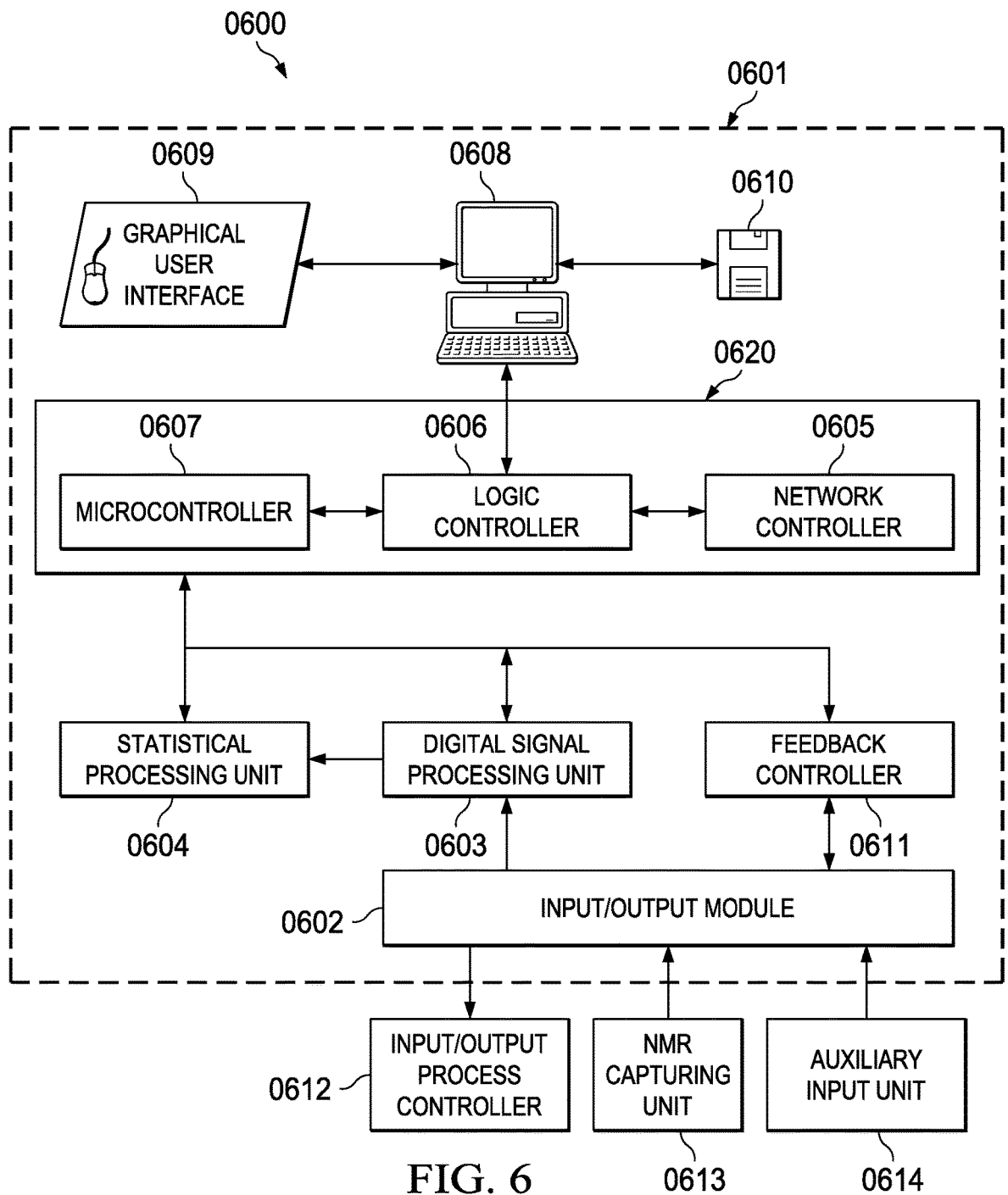
FIG. 6 is a data processing unit according to an exemplary embodiment of the present invention.

As generally illustrated in FIG. 6 (0600), a data processing unit (DPU) (0601) comprises a control unit (0620), a display unit, a processing unit and an input output module (0602). The control unit may further comprise a microcontroller (0607), a logic controller (0606), and a network controller (0605). The display unit may be connected to the control unit via a host bus. The display unit may further comprise a display terminal (0608) that is configured to display a graphical user interface (GUI) (0609). The GUI (0609) may be navigated with a pointing device or through a keyboard connected to the DPU. The GUI (0609) may be used to input parameters such as food snack specific properties, RF capture time, conveyor speed, NMR parameters and so on.

The processing unit may include a digital signal processing unit (0603) and a statistical processing unit (0604). The digital signal processing unit (0603) may receive input from an input-output module (0602). The statistical processing unit (0604) may receive input from the digital processing unit (0603) and further process the input. When a sensor receiver captures an NMR signal, the signal may be forwarded to the DPU (0601) via the input-output module (0602). The NMR signal may be forwarded to the DPU (0601) with a wired or a wireless connection. The connection protocol and connecting conducting wires may be chosen such that there is minimum loss of signal and the signal to noise ratio is acceptable for further processing. A general purpose bus may carry data to and from different modules of the DPU. It should be noted that the operation of the bus is beyond the scope of this invention.

The microcontroller (0607) may perform instructions from a memory or a ROM (0610). The instruction set of the microcontroller may be implemented to process the data of the NMR signal. A custom instruction set may also be used by the microcontroller to prioritize and expedite the processing of the NMR signal in real time during a manufacturing operation. The customization of the instruction set is beyond the scope of this invention. The logic controller may perform operations such as sequencing, prioritization and automation of tasks. The logic controller may also oversee the hand shake protocol for the bus interface. The microcontroller may display the food attribute information on the display (0608) via GUI (0609). The logic controller may further continuously monitor the state of input devices and make decisions based upon a custom program to control the state of output devices.

According to an exemplary embodiment, a feedback controller controls an input/output controller to adjust parameters to food processing modules such that the resultant output properties of the food snacks from the food processing modules fall within an acceptable range. As generally illustrated in FIG. 6 (0600), during a manufacturing process, food snack conveyed on a belt are struck with an RF pulse from a pulsing device. The resulting NMR signal may be captured by an NMR capturing unit (0613) and forwarded to the input/output module (0602). The input/output module (0602) may further forward the NMR signal to the digital signal processing unit (DSP) (0603) which processes the NMR signal.

The DSP (0603) may further comprise a smoothing module, a data transformation module, a signal to noise enhancing module and a normalization module.

According to a preferred exemplary embodiment, the signal smoothing module receives input from an input-output module (0602) in a data processing unit and smoothens the received raw NMR signal. The data transformation module may transform the signal using an inverse Laplace transform method. The data is made continuous by applying a windowing function to the discrete data. Windowing functions that may be applied to the discrete data may include Barlett, Blackmon, FlatTop, Hanning, Hamming, Kaiser-Bessel, Turkey and Welch windowing functions. A smoothing window with good frequency resolution and low spectral leakage for a random signal type may be chosen to smoothen the data. It should be noted that any commonly known windowing function may be applied to a raw NMR signal to smoothen and interpolate the raw NMR data.

The transformed frequency signal from the transformation module may be noisy. A signal to noise enhancement module may receive the transformed signal from the data transform module and enhance the signal-to-noise ratio of the signal for further processing. A predictive model for each input attribute (moisture, solids) of a food product may be input into the DPU (0601). The food attribute may be measured with a method as described previously and in FIG. 9 (0900). The micro controller (0607) may then direct a signal to instruct the feedback controller (0611) so that a controller to the units of a food processing unit or food pre-processing unit adjusts input parameters of the food processing unit or food pre-processing unit. Depending on the instructions from the microcontroller (0607), the feedback controller (0611) may communicate with an input/output process controller (0612). The input/output process controller (IOC) (0612) may be a conventional process control device such as PI, PID or a PD controller. Advanced process control techniques such as predictive controls techniques, fuzzy logic, inferential techniques, constant model predictive control (CMPC), multiple input multiple output (MIMO), single input multiple output (SIMO), single input single output (SISO), and supervisory control element that ultimately provides a set point may be used in conjunction with the IOC (0612). The IOC (0612) may adjust the input parameters such as input temperature, dwell time to food processing units such as a fryer. The IOC (0612) may also adjust the input parameters such as slice thickness to food pre-processing units such as a food slicer. An auxiliary input unit (0614) may further provide information from various sensors such as sensing technology based on infrared or near infrared spectroscopy, visible light, ultrasonics, electrical impedance and so on.

A statistical processing unit (SPU) (0604) may further comprise a subset regression module. The smoothened, transformed and normalized signal from the digital signal processing unit (0603) is forwarded to SPU (0604) for developing coefficients with good correlation for measuring a food attribute such as moisture and solids content. An $R^2$ value greater than 0.7 may be considered a good correlation between the measure value from the model and TGA measured number.

Figure 9:
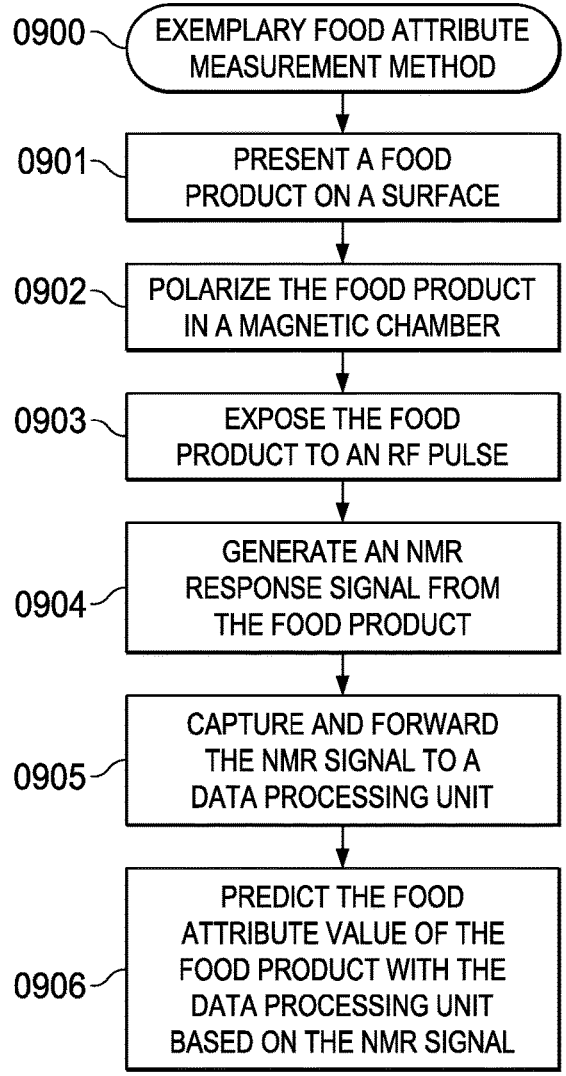
FIG. 9 is a general flow chart method for quantitative measurement of a food attribute with an NMR based apparatus according to an exemplary embodiment of the present invention.

As generally shown in FIG. 9, an exemplary food attribute measurement method may be generally described in terms of the following steps:
(1) presenting a food product (0901);
  The food may be presented on a surface which may be moving or stationary. The food product may be a raw potato or a bunch of potatoes. Alternatively, the food product may be a starch based food snack, legumes, pulses, corn, oats, cut fruits, whole fruits, tubers, or vegetables. Otherwise, the food product may be a starch based food snack, non-starch based food snack or seafood
(2) polarizing the food product in a magnetic chamber (0902);
  the polarizing step may range for a period of 0.3 second to 1 minute.
(3) exposing the food product to an RF pulse or sequence of pulses (0903);
  The duration of RF exposure may range for a period of 1 microsecond to 2 seconds.
(4) generating an NMR response signal from the food product (0904);
  The NMR signal may be detected from different locations within the food product, and may exhibit different temporal behavior and information content depending on the type of NMR methods employed.
(5) capturing and forwarding the NMR signal to a data processing unit (0905); and
(6) predicting the food attribute of the food product with the data processing unit (0906).
  The food attribute may be moisture content, solids content, reducing sugars, or total sugars in a food snack. A relaxation step may be included after the exposing step. The food attribute may be moisture percentage, absolute moisture content, solids content, absolute solids content, sugar percentage or absolute sugar content. Predictions may be based on either analytical or empirical methods.

This general method summary may be augmented by the various elements described herein to produce a wide variety of invention embodiments consistent with this overall design description.

Figure 10:
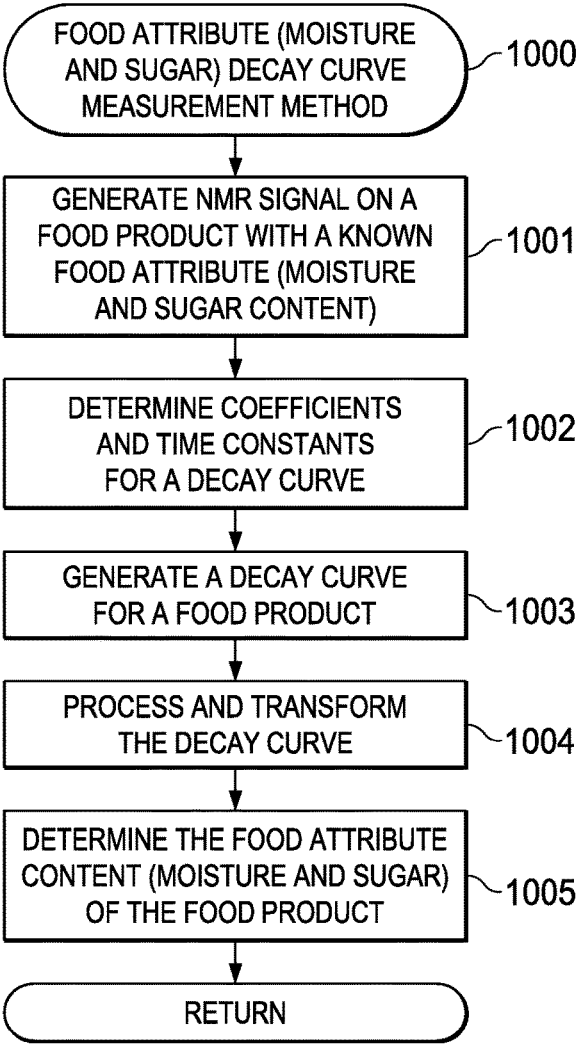
FIG. 10 is an exemplary flow chart method for the quantitative measurement of a food attribute using empirical predictions formulated from NMR decay curves generally defined by equations (1), (3), or (4). Typical NMR decay curves from potatoes are shown in FIG. 7 and FIG. 11.

The empirical approach illustrated in FIG. 10 employs the NMR decay curve of equations (1), (3), or (4) to predict a food attribute (moisture, solids, sugars) using the following steps:
(1) generating NMR signal from food products with known food attributes (moisture and sugar content) (1001);
(2) determining coefficients and time constants for a decay curve (1002);
(3) generating an NMR signal for a food product with unknown food attributes (1003);
(4) processing and transforming the decay curve, with the DPU (1004); and
(5) Determine the food attribute content (moisture and sugar) of the food product based on the coefficients determined in step 2 (1005).

This general empirical approach or method summary may be augmented by the various elements described herein to produce a wide variety of invention embodiments consistent with this overall design description. This includes multi-modal sensor approaches that combine NMR data with complimentary information obtained using other established sensor paradigms.

Figure 11:
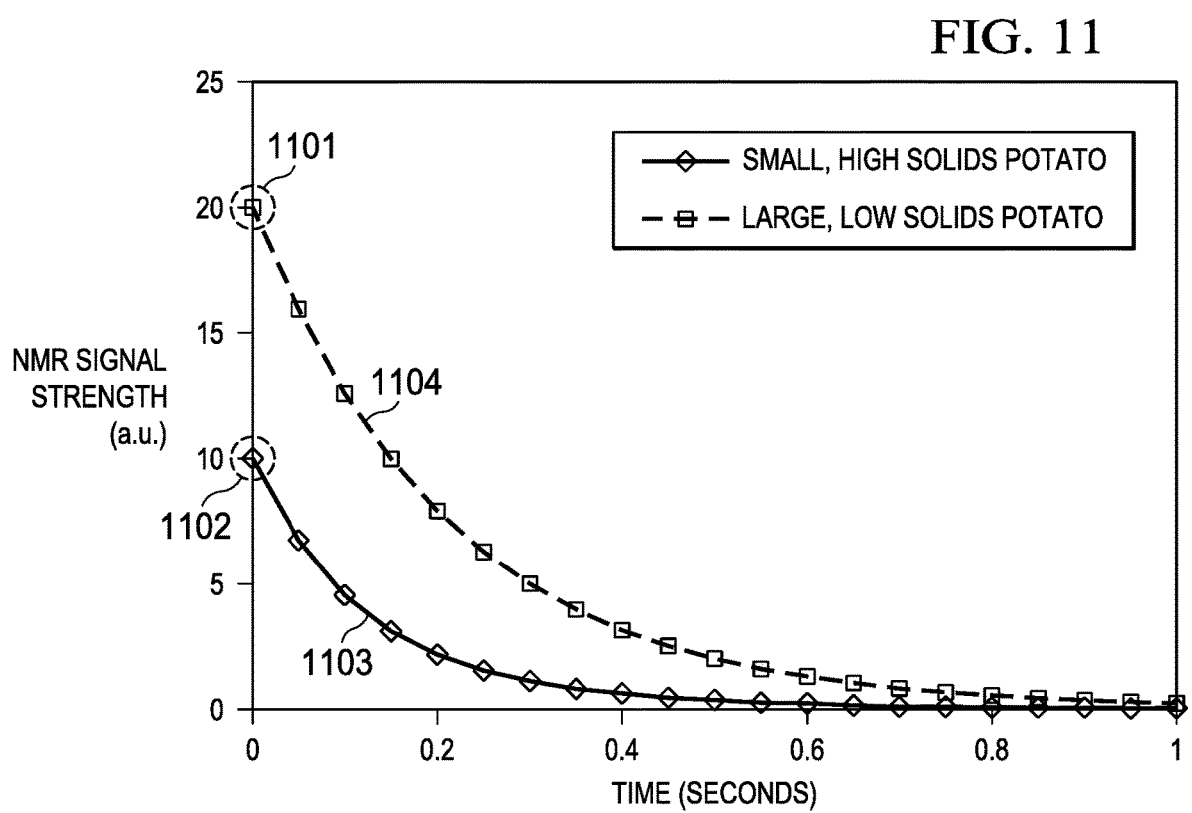
FIG. 11 is an exemplary decay curve generated from an NMR based apparatus according to a preferred embodiment of the present invention.

FIG. 11 generally illustrates a decay curve for food product generated with an NMR based apparatus. The Y-axis shows an NMR signal strength (S) plotted against time (t) on the X-axis. Two decay curves, one each for a small high solids potato (1103) and a large low solids potato (1104), are shown in FIG. 11. Each of the curves (1103, 1104) has a portion that intercepts the Y-axis at 1102 and 1101 respectively. The intercepts (1102, 1101) at time zero of the curves generally correlate to the total moisture content in the measured food snack. The solids or dry matter can be calculated based on the moisture content when the total mass of the snack product is known. Any food product can therefore be passed through an NMR apparatus and a decay curve similar to curve (1103) or (1104) may be generated. The moisture content can therefore be calculated from the curve when a suitable calibration is performed using samples with known moisture to relate S(t=0) to moisture weight.

Figure 12:
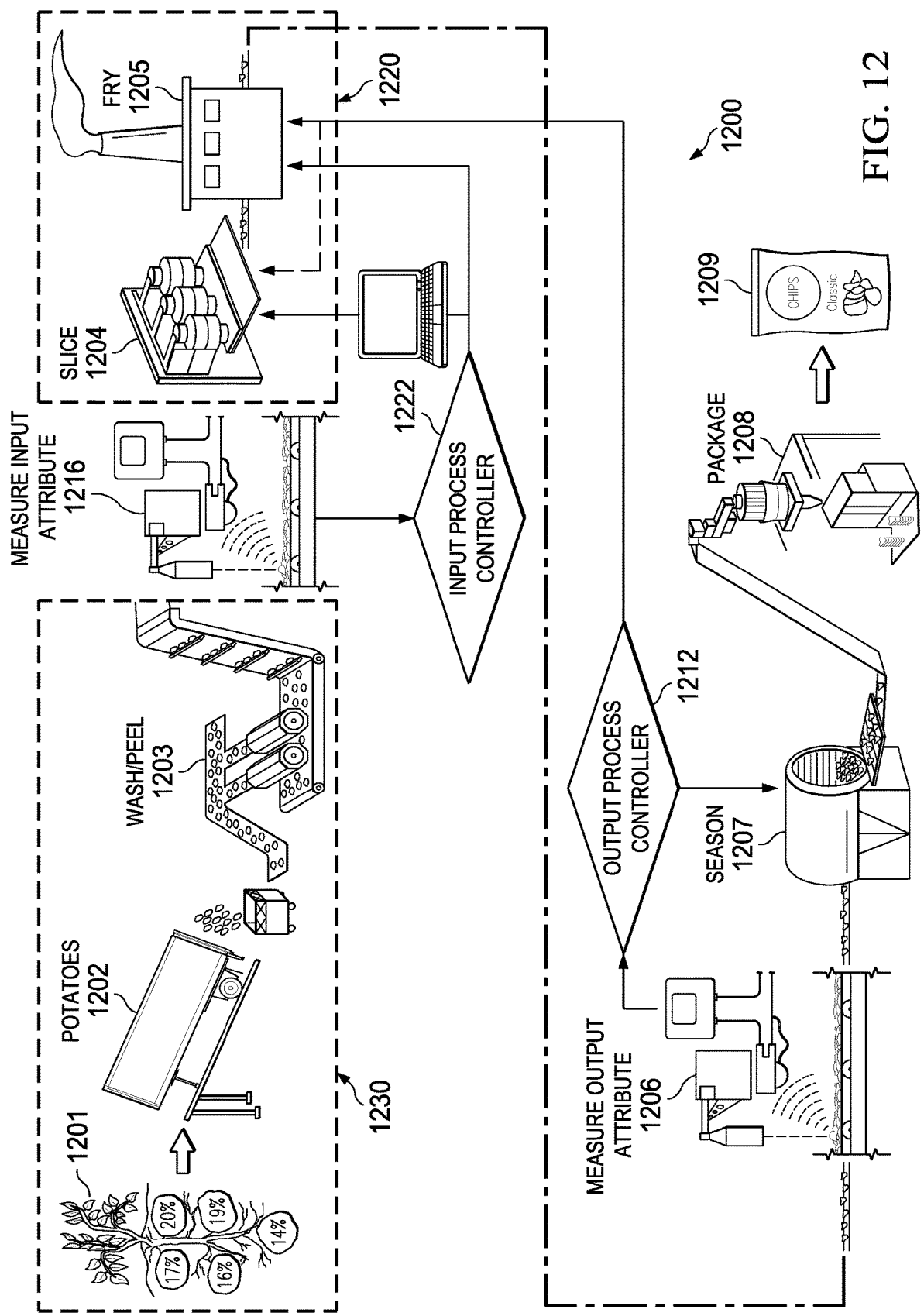
FIG. 12 is an exemplary quantitative food attribute combined feedback and feedforward manufacturing system according to a preferred embodiment of the present invention.

As generally illustrated in FIG. 12, an exemplary food snack manufacturing feedforward-feedback system comprises an input food attribute NMR based measurement tool (1216) that is positioned downstream of a food pre-processing unit (FPU) (1230) and upstream of a food processing unit (FPU) (1220). The system (1200) illustrated in FIG. 12 (1200) may be used to manufacture potato chips and other generally manufactured food products such as potato chips, tortilla chips, corn chips or any starch based food snacks. The manufacturing system may comprise a series of interconnected stations that include a sourcing stage (1201), a storage station (1202), wash/peel station (1203), slicing station (1204), frying station (1205), output food property measurement station (1206), a seasoning station (1207), a packaging station (1208) and a labeling station (1209). The food snacks, such as potato chips, may be conveyed from station to station on a conveyor belt in the manufacturing system. The storage station (1202), a food ingredient pre-treatment unit, and the wash/peel station (1203) may be combined as a food preprocessing unit (1230). The food preprocessing unit (1230) may also comprise one or a combination of the storage station (1202), a food ingredient pre-treatment unit, and the wash/peel station (1203). It should be noted that the food preprocessing unit may comprise other processing units ordinarily used in the food snack manufacturing. The FPU (1220) may include one or more of the processing units such as slicing station (1204) and frying station (1205). The input food attribute NMR based tool (1216) may be placed between any two stations in the manufacturing process to capture NMR signals from the passing product after RF exposure. For example, the measurement tool (1216) may be placed in between any two stations that may include sourcing stage (1201), storage station (1202), wash/peel station (1203), slicing station (1204), and frying station (1205). The slicing station (1204) may be connected to a slicing process controller (1212) that controls input parameters to the slicing station (1204) such as slicing thickness, moisture control, solids content and slicing ridges. The frying station (1205) may be connected to a fryer process controller (1211) that controls input parameters to the frying station (1205) such as oil input temperature, oil output temperature, oil volume, and frying dwell time. An in-line feedforward control with input food attribute quantitative NMR based measurement tool may enable a consistent repeatable and reproducible manufacturing output food property quality. The food properties may include solids content, moisture, density, oil content, slice thickness, seasoning particle size, and elements such as sodium, calcium, copper, zinc, magnesium, and potassium. According to a preferred exemplary embodiment, the quantitative food attribute measurement tool (1216) may be positioned immediately downstream of a food preprocessing unit (1230) and upstream of the FPU (1220). According to a preferred exemplary embodiment, the input food attribute measurement tool (1216) records/captures NMR signal when a pulsing device (RF) exposes the food ingredients from the food preprocessing unit (1230) to RF fields and processes the NMR signal to quantitatively measure an input food attribute. The pulsing device may strike the food product and produce an NMR signal as aforementioned in FIG. 4.

The (empirical) equation (2) for NMR predicted moisture may be developed using the method described in FIG. 10 (1000). The coefficients and time constants may be programmed into the measuring tool (1216) for measuring one or more input food attributes of food ingredients such as ingredient solids content, moisture content, sugar content and model an output food property attribute such as hardness, fracturability and denseness.

For example, in a potato chip manufacturing process, input ingredients such as potatoes may be modelled for input attributes such as input solids content, sugar content, moisture, density, and slice thickness. Potatoes may be procured from various farms and may possess varying moisture, sugar, and solid contents. The input measuring tool (1216) measures the attributes of the potatoes and programs an input controller that adjusts process variables to the food processing unit (1220) such that the output food property attribute of the produced potato chips falls within an acceptable limit. The input attributes may be provided to a data processing unit in an input food attribute measuring tool. The input attribute measurement tool (1216) may calculate an expected food property attribute such as hardness from with a correlation equation.

According to a preferred exemplary embodiment, depending on the measured input attribute, an input controller (1222) may control the output food property of a food product from the FPU (1220). The input controller (1222) may be connected to a slicing input controller and a frying input controller. Typical process control equipment such as PI and PID control devices, may be used to program the input parameters of the slicing station (1204) and frying station (1205). For example, if the expected output texture attribute based on a measured input attribute (moisture) falls outside an acceptable limit, the input controller (1222) may program an input parameter or a combination of input parameters (process variables) to the frying unit such as frying temperature or frying time. The input controller (1222) may program an input parameter to the slicing unit so that the slices are thinner or thicker depending on the correlation of the output attributes to the input food attributes. According to a preferred exemplary embodiment, the input food attribute measuring tool (1216) continuously feeds input attribute information to an input controller to program input parameters to the food processing unit (1220) such that the expected output food property attribute of the food product falls within an acceptable limit. The acceptable limit may be determined by desired food properties in a finished food product such as crispiness, freshness, oil content, etc. A tighter acceptable limit may indicate a more controlled quality process. The acceptable limit may also be further tuned as more data is collected. Each output food property attribute may have its own acceptable limits. The measured food property attributes may be monitored continuously and charted for sustaining process quality control. A statistical process control chart may be used to monitor and control a food property attribute with an upper limit and a lower limit. Any trends and outliers from the statistical process control chart may be used to correct, adjust, and detect potential issues with the processing units.

Furthermore, an output food property measurement tool (1206) may be positioned downstream of food processing unit (1220). The output food property measurement tool (1206) may be similar to the input food attribute measurement tool (1216). According to a preferred exemplary embodiment, depending on the measured output food property attribute, an output controller (1212) may control the output food property attribute of a food product from the FPU (1220). The output controller (1212) may be connected to a slicing input controller and a frying input controller. Typical process control equipment such as PI, PID control devices, may be used to control the input parameters of the slicing station (1204) and frying station (1205). For example, if a texture attribute, such as hardness, falls outside an acceptable limit, the output controller (1212) may adjust an input parameter to the frying unit such as frying temperature or frying time. The output controller (1212) may adjust an input parameter to the slicing unit so that the slices are thinner or thicker depending on the correlation of the output texture attribute to the input parameters. According to a preferred exemplary embodiment, the input food attribute measuring tool (1206) continuously feeds back information to control input parameters to the food processing unit (1220) such that the output food property attribute of the food product falls within an acceptable limit.

According to a preferred exemplary embodiment, the output food property measurement tool may heuristically train the input measurement tool such that the output food property attributes of the food product from the food processing unit is tightly controlled. The output food property measurement tool (1206) may feed information to input measurement tool (1216) so that the input parameters (process variables) to the food processing unit are continuously adjusted in order to tightly control the output food property attribute. This is especially important as new batches of food ingredients with varying attributes are input to the food preprocessing unit that may impact the output food property of the food product. The continuous feedforward and feedback loop enable a substantially tighter control on the output food property in addition to significant reduction of wastage due to unacceptable food property of the produced food product. According a preferred exemplary embodiment, the tighter control limits may be within +−20% of the output food property attribute limit. According to a more preferred exemplary embodiment, the tighter control limits may be within +−10% of the output food property attribute limit. According to a most preferred exemplary embodiment, the tighter control limits may be within +−5% of the output food property attribute limit.

Figure 13:
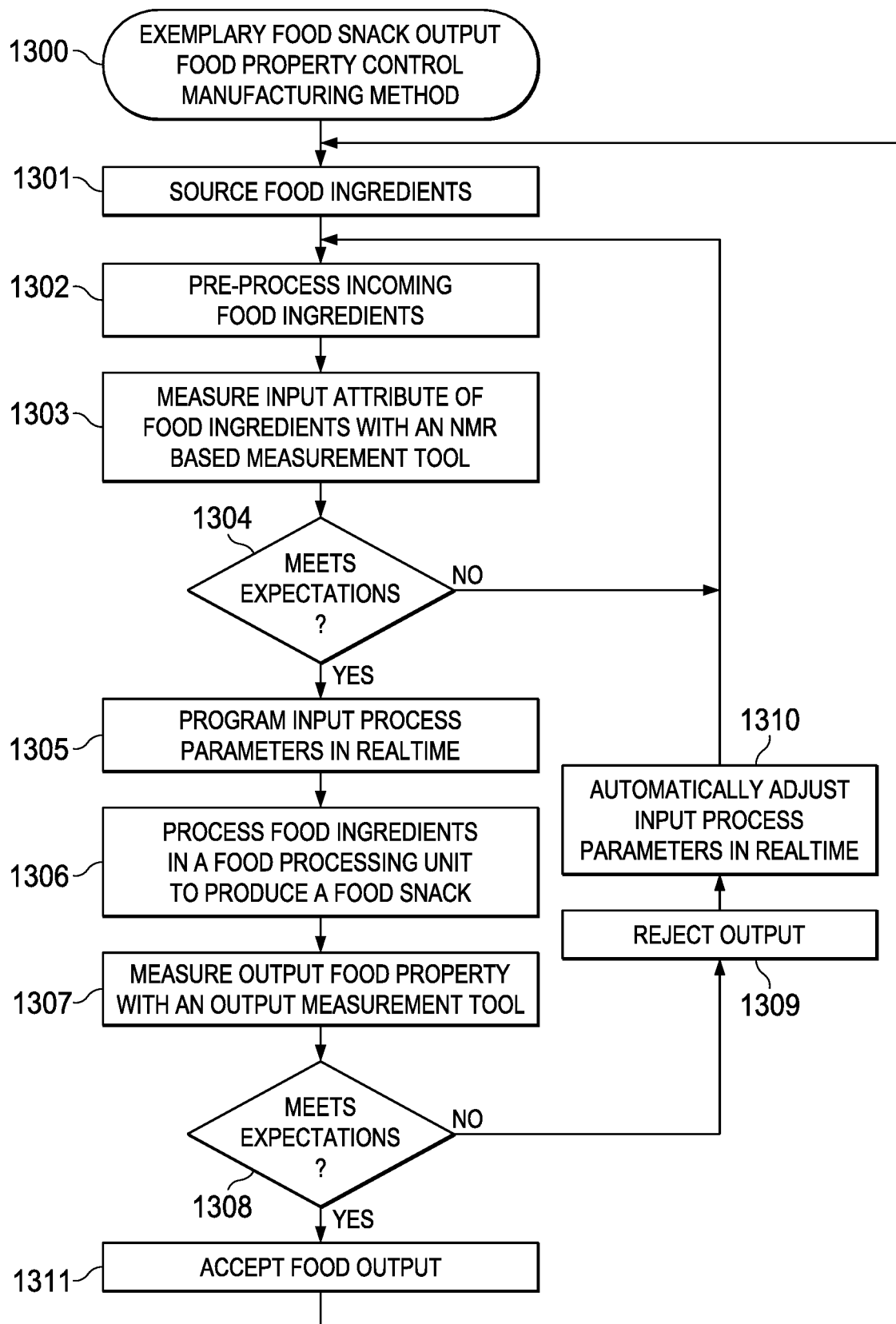
FIG. 13 is an exemplary quantitative food attribute combined feedback and feedforward manufacturing method according to a preferred embodiment of the present invention.

As generally shown in FIG. 13, an exemplary feedforward and feedback manufacturing method associated with the feedback manufacturing system in FIG. 12 may include the steps comprising:
(1) Sourcing food ingredients (1301);
 The food ingredients may be potatoes that may be procured from different sources.
(2) pre-processing food ingredients in a food pre-processing unit (1302);
(3) measuring an input attribute of the food ingredients with an NMR based measuring tool (1303);
(4) with an NMR based measuring tool, determining if an expected output food property attribute based on the measured input attribute is within an acceptable limit, if not, rejecting the input food ingredients and proceeding to step (2) (1304);
 The input attribute may be food properties such as moisture content and solids content.
(5) program input parameters (process variables) to a food processing unit (1305);
(6) processing food ingredients in a food processing unit to produce a food product (1306);
(7) measuring output food property attribute with an output food property measuring tool (1307);
(8) determining if the output food property attribute is within an acceptable limit, if so, proceeding to step (11) (1308);
(9) if the food property attribute is outside an acceptable limit in step (1308), rejecting the food product (1309);
(10) feeding back output food property attribute information to a controller to adjust input parameters to the food processing unit, proceeding to step (2) (1310); and
(11) accepting the food product and proceeding to step (1) (1311).

This general method summary may be augmented by the various elements described herein to produce a wide variety of invention embodiments consistent with this overall design description.

In some cases the NMR experiment used to generate signal in equations (1), (3), or (4) has a limited ability to detect fast decaying signal components. When this is true, quickly decaying NMR signal is more commonly detected with a different class of NMR experiments leading to equation (5). Under these circumstances it is possible to estimate the amount of fast decaying signal from the data measured with both types of experiments. In food products or their raw materials, such signal may be commonly attributed to bound water that is tightly associated with relatively immobile surfaces in small pores or on large biomolecules. Practical methods for distinguishing bound water may therefore be employed for monitoring important changes occurring at the microscopic and molecular scales. One exemplary method is described in FIG. 14 and consists of the following steps:
(1) Measure total moisture content (first moisture content) in the food product with the first NMR-based apparatus (1401);
 The first NMR-based apparatus may generate signal defined by equation (5) and the apparatus may be the NMR-based apparatus described in FIG. 4 (0400). In this case total moisture content is determined from $A_{total}$ in equation (5).
(2) Measure the moisture content (second moisture content) in the food product with a second NMR-based apparatus (1402);
 The second apparatus may be another NMR-based apparatus like FIG. 4 (0400) or FIG. 5 (0500), but in this case, generated NMR signal is defined by equations (1), (3), or (4). If the apparatus of FIG. 5(0500) is used, a mass flow device may be attached to the apparatus. Moisture content from this second measurement is then determined from $S(t=0)$. More generally, the apparatus of step (1401) and step (1402) may be the same if the food product is measured on the same device two separate times using the NMR methods described above. According to another preferred exemplary embodiment, the types of signal measured with the first and second apparatus is switched to create an opposite order.
(3) Calculate the bound moisture content based on a difference or ratio between the first moisture content and the second moisture content.
 The bound moisture may be based on a difference of NMR signal $(A_{total}-S(t=0))$ measured from step (1401) and step (1402). Alternatively, a bound water fraction may be calculated as $(A_{total}-S(t=0))/A_{total}$. The bound (or unbound) moisture content may then be used to correlate to several of the food attributes in a final product such as texture, flavor, and color. It also possible to control the food attributes in a final product by controlling the unbound moisture. It should be noted that the terms bound/unbound, freezeable/unfreezeable moisture content refer to a moisture content that is bound and unbound in a food product.

This general method summary may be augmented by the various elements described herein to produce a wide variety of invention embodiments consistent with this overall design description. It is also noted that bound and unbound water compartments may also be distinguished using a single NMR experiment that generates signal defined by equations (1), (3), or (4), and is properly configured to detect fast decaying components. Envisioned embodiments for measuring bound or unbound water therefore includes alternative NMR approaches.

FIG. 15 (1500) generally shows a graph of how the fraction (f) of detectable water (1502) varies as a function of TGA dry-matter (1501). Within the context of FIG. fraction (f) may be defined as $f=S(t=0)/A_{total}$. The fraction (f) of detectable water may therefore be interpreted as the ratio of unbound water to total water (unbound+bound). The basic idea is that different NMR methods capture different amounts of water depending on the rate of NMR relaxation (B) and experimental time-scales. Under certain conditions, methods leading to equations (1), (3), or (4) only capture the more mobile (unbound) water; whereas, methods leading to equations (5) and (6) typically capture all water types independent of mobility and relaxation rate. For example, if the total moisture in a potato is 10 grams, a fraction (f) of 0.9 indicates that 9 grams of the total moisture is detectable (unbound) from S(t=0) and 1 gram is not detectable due to fast relaxing or bound components. The chart (1500) clearly shows that NMR methods leading to equations (1), (3), or (4) do not always account for all of the moisture in the food product i.e., the fraction (f) is less than 1. The same results also show that the fraction (f) is highly predictive of dry matter content measured with TGA. It should be understood that predictions of dry matter or other food attributes can be based on a host of alternative bound/unbound water metrics, including—$(A_{total}-S(t=0))/A_{total}$, or more elaborate analysis based on the inverse Laplace transform of equation (4). The important point is that empirical methods exploiting bound/unbound water compartments can give highly predictive results that only require NMR data and no additional sensor input (i.e. without independent mass measurements).

According to another preferred exemplary embodiment the NMR signal defined by equation (1) captures fast decay signal characteristic of bound water and other solid compounds comprising carbohydrates, starches and the like. According to another preferred exemplary embodiment, the NMR signal from solid and water constituents is differentiated to directly estimate moisture and/or solids content without the need for additional mass measurements. According to another preferred exemplary embodiment multivariate prediction models may be created that include NMR parameters for bound and unbound water, as well as different solid constituents.

System Summary

The present invention system anticipates a wide variety of variations in the basic theme of a non-invasive quantitative food attribute measurement of a food product, the apparatus comprising: a magnetic chamber; a pulsing device attached to the magnetic chamber; a sensor receiver attached to the magnetic chamber; a data processing unit in communication with at least the sensor receiver; wherein the pulsing device is configured to expose the food product to RF fields, thereby producing an NMR response signal to be detected by the sensor receiver; wherein further the data processing unit is configured to quantitatively measure the food attribute of the food product based on the NMR response signal from the sensor receiver.

This general system summary may be augmented by the various elements described herein to produce a wide variety of invention embodiments consistent with this overall design description.

Method Summary

The present invention method anticipates a wide variety of variations in the basic theme of implementation, but can be generalized as a non-invasive method for measuring a food attribute of a food product, the method comprises the steps of:
a) presenting a food product on a surface;
b) polarizing the food product in a magnetic chamber;
c) exposing the food product to an RF pulse;
d) generating an NMR response signal from the food product;
e) capturing and forwarding the NMR signal to a data processing unit; and
f) predicting the food attribute with the data processing unit Feedforward-Feedback Control System Summary The present invention system anticipates a wide variety of variations in the basic theme of controlling a food attribute of a food product in a continuous manufacturing process, wherein the system comprises:
a food pre-processing unit;
a food processing unit;
a food attribute measuring tool positioned downstream from the food pre-processing unit, wherein the food attribute measuring tool is configured to quantitatively measure an attribute of food ingredients that are input to the food
processing unit, by application of RF pulses on at least a portion of the food ingredients and a sensor receiver to capture an NMR signal generated by the applied RF; and
a controller, the controller controlling a plurality of input parameters to the food processing unit and the food pre-processing unit based on the above food attribute measuring tool.

This general system summary may be augmented by the various elements described herein to produce a wide variety of invention embodiments consistent with this overall design description.

Feedforward-Feedback Control Method Summary

The present invention method anticipates a wide variety of variations in the basic theme of implementation, but can be generalized as a feedforward-feedback method for controlling a food attribute of a food product with the above feedforward-feedback system. The method comprises the steps of:
(1) measuring an input attribute of food ingredients with a food attribute measuring tool;
(2) determining if the input attribute value is within an acceptable input limit, if so, proceeding to step (4);
(3) rejecting the food ingredients and proceeding to step (1);
(4) programming plural input parameters to a food processing unit based on the input attribute value;
(5) producing food product from the food processing unit; and
(6) measuring the food attribute and proceeding to step (1).

System/Method Variations

The present invention anticipates a wide variety of variations in the basic theme of measuring food attributes. The examples presented previously do not represent the entire scope of possible usages. They are meant to cite a few of many possibilities. The basic system and method may be augmented with a variety of ancillary embodiments, including but not limited to:
An embodiment wherein shape of the magnetic chamber is a hollow cylinder.
An embodiment wherein the magnetic chamber further comprises current carrying wire or permanently magnetized materials; the current carrying wire or the permanently magnetized materials are geometrically configured to expose the food product to a static magnetic field An embodiment wherein the food or food product is placed on a stationary surface where the food or food product is exposed to RF fields.

An embodiment wherein the food product is passing within the magnetic chamber when RF fields are applied.

An embodiment wherein the sensing device is configured to capture signal at or near the larmor frequency for the NMR response signal.

An embodiment wherein a distance between the signal sensing device and the food product ranges from 0.0 inch to 2 feet.

An embodiment wherein the food product is selected from a group comprising: a starch based food snack, legumes, pulses, corn, oats, cut fruits, whole fruits, tubers, and vegetables.

An embodiment wherein the food product is a starch based food snack.

An embodiment wherein the food product is a raw potato.

An embodiment wherein the food product is a finished food snack.

An embodiment wherein the data processing unit further comprises a digital signal processing unit and a food attribute computing unit.

An embodiment wherein the food attribute is selected from a group comprising: moisture percentage, absolute moisture content, sugar percentage or absolute sugar content.

An embodiment wherein the food product remains intact after the application of RF fields.

An embodiment wherein the sensor receiver is configured to be wired to the data processing unit.

An embodiment wherein the sensor receiver is configured to be wirelessly connected to the data processing unit.

An embodiment wherein the magnetic chamber is configured to generate magnetic field in a range of 1 Gauss to 6000 Gauss.

An embodiment is further configured with a mass flow device, the mass flow device configured to measure mass of the food product.

An embodiment wherein a percentage number or fraction of the food property is calculated based on a decay curve of the NMR signal.

One skilled in the art will recognize that other embodiments are possible based on combinations of elements taught within the above invention description.

What is claimed is:

1. A non-invasive method for measuring a food attribute of a food product, the method comprises:
    polarizing the food product as the food product is conveyed in a magnetic chamber configured (i) to use at least one low field magnet to provide a static magnetic field within the magnetic chamber, the static magnetic field having a magnetic field strength from 1 to 6000 Gauss, and (ii) to polarize the food product with the static magnetic field;
    exposing the food product to a radio frequency (RF) pulse, wherein the food product is moving when the RF pulse strikes the food product;
    generating a nuclear magnetic resonance (NMR) response signal from the food product;
    capturing information from the NMR response signal while the food product is moving and forwarding the information from the NMR response signal to a data processing unit;
    measuring a mass of the food product that is responsible for the NMR response signal, wherein the measuring is separate from the capturing information and is performed by an apparatus separate from an apparatus used to generate a NMR response signal;
    forwarding the measured mass to the data processing unit; and
    predicting the food attribute with the data processing unit based on the measured mass and the information in the NMR response signal, the information in the NMR response signal indicating an amount of hydrogen in liquids in the food product as differentiated from an amount of hydrogen in solids in the food product.

2. The method of claim 1 wherein the NMR response signal is detected from different locations within the food product.

3. The method of claim 1 wherein the food product is exposed to the RF pulse for a period of 1 microsecond to 60 seconds.

4. The method of claim 1 wherein the food product is polarized by the static magnetic field for a period of 0.3 second to 1 minute.

5. The method of claim 1 wherein the food product is selected from a group consisting of: a starch based food snack, a non-starch based food snack, and seafood.

6. The method of claim 1 wherein the food attribute is selected from a group consisting of: moisture percentage, absolute moisture content, solids content, absolute solids content, sugar percentage and absolute sugar content.

7. The method of claim 1, wherein the food product is selected from a group consisting of: a starch based food snack, legumes, pulses, corn, oats, cut fruits, whole fruits, tubers, and vegetables.

8. The method of claim 1, wherein the food product is at least one raw potato.

9. The method of claim 1, wherein the food product is a finished food snack.

10. The method of claim 1, wherein the food product remains intact after RF fields are applied.

11. The method of claim 1, wherein the food product is conveyed at 2 to 100 feet per minute within the magnetic chamber as the RF pulse is applied to the food product.

12. The method of claim 11, wherein the food product is polarized in the magnetic chamber for 0.3 to 5 seconds.

13. The method of claim 11, wherein the food product is polarized in the magnetic chamber for 1.5 to 2 seconds.

14. The method of claim 12, wherein the magnetic field strength is from 70 to 3000 Gauss.

15. The method of claim 14, wherein in step d) the NMR response signal is captured for 0.01 seconds to 3 minutes.

16. The method of claim 15, wherein in step d) the NMR response signal is captured for 0.2 to 5 seconds.

17. The method of claim 16, wherein in step d) the NMR response signal is captured for 0.2 to 1 second.

18. The method of claim 16, wherein the magnetic chamber acts as a Faraday cage during the method.

19. The method of claim 18, wherein the information comprises the Larmor frequency for the NMR response signal and frequencies above and below the Larmor frequency.

20. The method of claim 19, wherein the RF pulse has a pulse duration of 1 microsecond to 10 milliseconds.

21. The method of claim 20 wherein the food attribute of the food product is quantitatively measured based on the information in the NMR response signal that indicates the amount of hydrogen in liquids in the food product and the amount of hydrogen in solids in the food product.

22. The method of claim 20 wherein the food attribute is moisture content by weight.

23. The method of claim 20 wherein the food attribute is sugar content by weight.

24. The method of claim 20 wherein the method measures moisture content by weight and sugar content by weight.

25. The method of claim 1 wherein the food attribute of the food product is quantitatively measured based on the information in the NMR response signal that indicates the amount of hydrogen in liquids in the food product and the amount of hydrogen in solids in the food product.

26. The method of claim 1 wherein the method comprises measuring a percentage of moisture by weight in the food product using the NMR response signal and the measured mass of the food product that is responsible for the NMR response signal.

* * * * *